(12) United States Patent
Boland et al.

(10) Patent No.: US 7,051,654 B2
(45) Date of Patent: May 30, 2006

(54) INK-JET PRINTING OF VIABLE CELLS

(75) Inventors: Thomas Boland, Suwanee, GA (US); William Crisp Wilson, Jr., Easley, SC (US); Tao Xu, Clemson, SC (US)

(73) Assignee: Clemson University, Clemson, SC (US)

( * ) Notice: Subject to any disclaimer, the term of this patent is extended or adjusted under 35 U.S.C. 154(b) by 248 days.

(21) Appl. No.: 10/666,836

(22) Filed: Sep. 17, 2003

(65) Prior Publication Data

US 2004/0237822 A1 Dec. 2, 2004

Related U.S. Application Data

(60) Provisional application No. 60/474,469, filed on May 30, 2003.

(51) Int. Cl.
*B41J 2/17* (2006.01)

(52) U.S. Cl. .......................... 101/483; 347/146; 435/4; 435/29

(58) Field of Classification Search ................ 101/483; 347/46, 10, 12, 16, 19, 23, 58; 600/407; 435/7.2, 435/29, 395, 397; 463/164
See application file for complete search history.

(56) References Cited

U.S. PATENT DOCUMENTS

| | | |
|---|---|---|
| 4,247,279 A | 1/1981 | Masters |
| 4,291,992 A | 9/1981 | Barr et al. |
| 4,585,139 A | 4/1986 | Bronson et al. |
| 4,594,597 A | 6/1986 | Liu et al. |
| 4,646,106 A | 2/1987 | Howkins |
| 4,665,492 A | 5/1987 | Masters |
| 4,673,304 A | 6/1987 | Liu et al. |
| 4,772,141 A | 9/1988 | Sanders, Jr. et al. |
| 4,889,438 A | 12/1989 | Forsyth et al. |
| 4,896,980 A | 1/1990 | Sanders, Jr. et al. |
| 4,921,365 A | 5/1990 | Sanders, Jr. et al. |
| 4,948,280 A | 8/1990 | Sanders, Jr. et al. |
| 4,969,758 A | 11/1990 | Sanders, Jr. et al. |
| 4,980,112 A | 12/1990 | Masters |
| 5,016,121 A | 5/1991 | Peddle et al. |
| 5,039,297 A | 8/1991 | Masters |
| 5,040,911 A | 8/1991 | Sanders, Jr. et al. |
| 5,075,805 A | 12/1991 | Peddle et al. |
| 5,134,569 A | 7/1992 | Masters |
| 5,204,055 A | 4/1993 | Sachs et al. |
| 5,216,616 A | 6/1993 | Masters |
| 5,490,962 A | 2/1996 | Cima et al. |
| 5,492,937 A | 2/1996 | Bogentoft et al. |
| 5,546,313 A | 8/1996 | Masters |
| 5,599,695 A | 2/1997 | Pease et al. |
| 5,605,662 A | 2/1997 | Heller et al. |
| 5,658,802 A | 8/1997 | Hayes et al. |
| 5,694,324 A | 12/1997 | Masters et al. |
| 5,702,717 A | 12/1997 | Cha et al. |
| 5,739,832 A | 4/1998 | Heinzl et al. |
| 5,797,898 A | 8/1998 | Santini, Jr. et al. |
| 5,798,779 A * | 8/1998 | Nakayasu et al. ............ 347/46 |
| 5,831,070 A | 11/1998 | Pease et al. |

(Continued)

OTHER PUBLICATIONS

Article—*Cell and Organ Printing 1: Protein and Cell Printers*, W. Cris Wilson, Jr. and Thomas Boland, The Anatomical Record Part A, vol. 272A, 2003, pp. 491–496.

(Continued)

*Primary Examiner*—Eugene H. Eickholt
(74) *Attorney, Agent, or Firm*—Dority & Manning, P.A.

(57) ABSTRACT

A method for forming an array of viable cells is provided. In one embodiment, the method comprises ink-jet printing a cellular composition containing cells onto a substrate. Upon printing, at least about 25% of the cells remain viable after incubation for 24 hours at 37° C. in a 5% $CO_2$/95% $O_2$ environment.

90 Claims, 14 Drawing Sheets

U.S. PATENT DOCUMENTS

| | | |
|---|---|---|
| 5,929,208 A | 7/1999 | Heller et al. |
| 6,087,102 A | 7/2000 | Chenchik et al. |
| 6,103,528 A | 8/2000 | An et al. |
| 6,109,717 A | 8/2000 | Kane et al. |
| 6,123,861 A | 9/2000 | Santini, Jr. et al. |
| 6,132,468 A | 10/2000 | Mansmann |
| 6,139,831 A | 10/2000 | Shivashankar et al. |
| 6,171,797 B1 | 1/2001 | Perbost |
| 6,197,575 B1 | 3/2001 | Griffith et al. |
| 6,239,273 B1 | 5/2001 | Pease et al. |
| 6,261,493 B1 | 7/2001 | Gaylo et al. |
| 6,336,480 B1 | 1/2002 | Gaylo et al. |
| 6,341,952 B1 | 1/2002 | Gaylo et al. |
| 6,387,707 B1 * | 5/2002 | Seul et al. .................. 436/164 |
| 6,394,585 B1 | 5/2002 | Ross |
| 6,402,403 B1 | 6/2002 | Speakman |
| 6,419,883 B1 | 7/2002 | Blanchard |
| 6,451,346 B1 | 9/2002 | Shah et al. |
| 6,454,811 B1 | 9/2002 | Sherwood et al. |
| 6,455,311 B1 | 9/2002 | Vacanti |
| 6,495,102 B1 | 12/2002 | Suslick et al. |
| 6,497,510 B1 | 12/2002 | Delametter et al. |
| 6,514,518 B1 | 2/2003 | Monkhouse et al. |
| 6,527,378 B1 | 3/2003 | Rausch et al. |
| 6,536,873 B1 | 3/2003 | Lee et al. |
| 6,536,895 B1 | 3/2003 | Kashiwagi et al. |
| 6,538,089 B1 | 3/2003 | Samra et al. |
| 6,543,872 B1 | 4/2003 | Ohtsuka et al. |
| 6,547,994 B1 | 4/2003 | Monkhouse et al. |
| 6,548,263 B1 * | 4/2003 | Kapur et al. .................. 435/7.2 |
| 6,550,904 B1 | 4/2003 | Koitabashi et al. |
| 6,561,626 B1 | 5/2003 | Min et al. |
| 6,561,642 B1 | 5/2003 | Gonzalez |
| 6,565,176 B1 | 5/2003 | Anderson et al. |
| 6,573,063 B1 * | 6/2003 | Hochman ................... 435/29 |
| 2002/0031500 A1 | 3/2002 | MacLaughlin et al. |
| 2002/0059049 A1 | 5/2002 | Bradbury et al. |
| 2002/0064808 A1 | 5/2002 | Mutz et al. |
| 2002/0064809 A1 | 5/2002 | Mutz et al. |
| 2002/0084290 A1 | 7/2002 | Matema |
| 2002/0089561 A1 | 7/2002 | Weitzel et al. |
| 2002/0090720 A1 | 7/2002 | Mutz et al. |
| 2002/0106412 A1 | 8/2002 | Rowe et al. |
| 2002/0160109 A1 | 10/2002 | Yeo et al. |
| 2002/0173586 A1 | 11/2002 | Jeong et al. |
| 2003/0003575 A1 | 1/2003 | Vacanti et al. |
| 2003/0032203 A1 | 2/2003 | Sabatini et al. |
| 2003/0059537 A1 | 3/2003 | Chilkoti et al. |
| 2003/0100824 A1 * | 5/2003 | Warren et al. .............. 600/407 |

OTHER PUBLICATIONS

Article—*Cell and Organ Printing 2: Fusion of Cell Aggregates in Three–Dimensional Gels*, Thomas Boland, Vladimir Mironov, Anna Gutowska, Elisabeth A. Roth, and Roger R. Markwald, The Anatomical Record Part A, vol. 272A, 2003, pp. 497–502.

Article—*Characterization of Patterned Self–Assembled Monolayers and Protein Arrays Generated by the Ink–Jet Method*, Laura Pardo, W. Cris Wilson, Jr., and Thomas Boland, Langmuir, vol. 19, No. 5, 2003, pp. 1462–1466.

Article—*Organ printing: computer–aided jet–based 3D tissue engineering*, Vladimir Mironov, Thomas Boland, Thomas Trusk, Gabor Forgacs, and Roger R. Markwald, TRENDS in Biotechnology, vol. 21, No. 4, Apr. 2003, pp. 157–160.

Article—*A Thermal Inkjet Printhead with a Monolithically Fabricated Nozzle Plate and Self-Aligned Ink Feed Hole*, Jae–Duk Lee, Jun–Bo Yoon, Jae–Kwan Kim, Hoon–Ju Chung, Choon–Sup Lee, Hi–Deok Le, Ho–Jun Lee, Choong–Ki Kim, and Chul–Hi Han, Journal of Microelectromechanical Systems, vol. 8, No. 3, Sep. 1999, pp. 229–236.

Article—*New inexpensive Technologies for Two and Three–dimensional Patterning of Proteins on Solid Supports*, W. C. Wilson, Jr. and T. Boland, Society for Biomaterials, 27th Annual Meeting Transactions, May 2001, 1 page.

Article—*Six Technologies that will Change the World*, David Pescovitz, Business 2.0, May 2003, 6 pages.

HP DeskJet 660C Printer—Printer Product Specifications, May 6, 2003, pp. 1–12.

HP DeskJet 550C Printer—Printer Product Specifications, May 5, 2003, pp. 1–6.

Data Sheet from Internet Entitled *Methods for Measuring Apoptotic Cell Death by Flow Cytometry*, www.cyto.purdue.edu, 1 page.

Data Sheet from Internet Entitled *HAT Capabilities*, www.sciperio.com, 2 pages, Apr. 22, 2003.

Information from Internet on Sciperio, Inc. collaborators, www.sciperio.com, 2 pages, Apr. 25, 2003.

Information from Internet—BBC News—Health entitled *Artificial tissue?*, www.bbc.co.uk, 4 pages, Jan. 23, 2003.

Article from Internet Entitled *Ink–jet printing creates tubes of living tissues*, NewScientist.com, Jan. 22, 2003, 2 pages.

Abstract—*High–Throughput Technologies for Cell Patterning and Quantitative Assaying*, T. Boland, W. C. Wilson, and L. F. Pardo, Publication of Abstract May 31, 2002, 2 pages.

Information from Internet—*Printing a heart*, Sara Abdulla, www.nature.com, Oct. 11, 1992, 2 pages.

* cited by examiner

☐ Percentage of imprinted bacterial colonies as related to the total dots designed.

■ Percentage of isolated bacterial colonies as related to the total imprinted bacterial colonies on the agar-coated slide.

1mm

2mm

 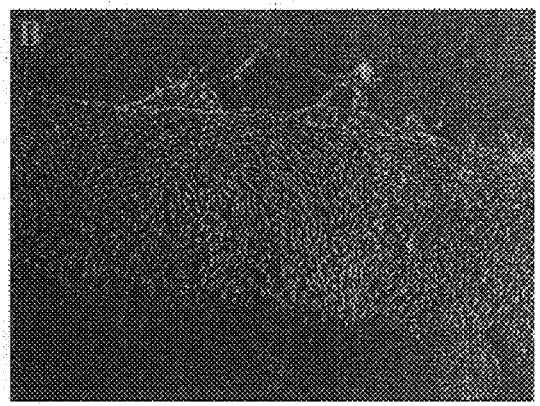
FIG. 13A    FIG. 13B
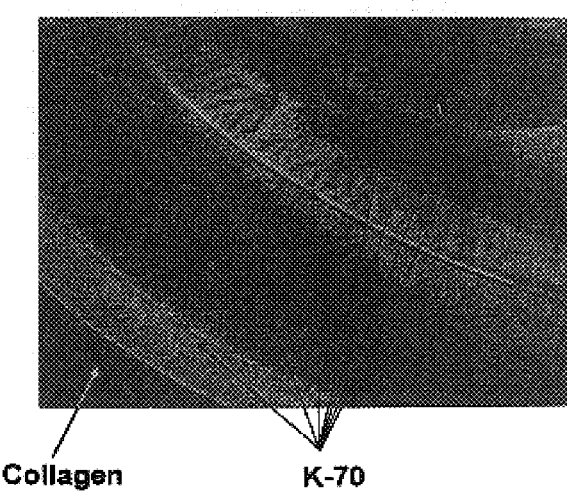
Collagen    K-70
FIG. 14

INK-JET PRINTING OF VIABLE CELLS

RELATED APPLICATIONS

The present application claims priority to U.S. Provisional Application Ser. No. 60/474,469, which was filed on May 30, 2003.

BACKGROUND OF THE INVENTION

Ink-jet printing is a non-contact reproduction technique that includes the acceptance of a digital signal representing an image and subsequent reproduction of the image onto a substrate by deposition of ink drops. Ink-jet devices typically include a printer head having one or more nozzles, each of which utilizes a static pressure ink reservoir, a small diameter orifice exiting the ink reservoir, and a voltage-gated orifice exiting the nozzle. The printer head is positioned using a two-dimensional translation mechanism. The volume of liquid dispensed in a drop is generally determined by the characteristics of the voltage-gated nozzle, while the lateral resolution of the device is usually determined by an encoder that senses the relative position of the nozzle and is controlled from a computer by a printer driver. It has been proposed to use ink-jet technology to deposit arrays of DNA-type polymers and proteins. Unfortunately, however, ink-jet printing applications have thus far been limited to non-viable biological materials. One reason for this limitation is that the high shear stresses (up to about 10 meters per second) and/or the high temperatures (up to about 300° C.) associated with ink-jet printing are believed to damage or kill viable cells. In addition, the outlet nozzles of the printer heads of most standard printers are too small to accommodate many viable cell sizes. Further, the feed mechanism of most commercially available ink-jet printers supplies paper in a circuitous route. Such circuitous systems are not always feasible when printing multiple layers or when printing onto a large, non-pliable substrate, such as a tray.

Instead, the deposition of viable cells is typically performed using robotic spotting systems, such as the Genetix Qbot system and the Beckman Coulter ORCA robot system. These systems are quite expensive and fairly slow, employing a multi-pin contact process that transfers bacteria onto a membrane filter substrate in ordered arrays with a gridding head of usually either 96 or 384 pins, which can grid up to about 3,456 colonies onto a single 8×12 centimeter substrate. Each pin is dipped into a corresponding well source plate where it picks up a target bacteria that is then directed onto the substrate. Washing and sterilization of the pins must be performed before the gridding head can be moved to new well source plates.

Techniques of forming arrays of viable cells become even more prohibitively expensive and slow when assembling cells in complex arrangements and/or when assembling more than one cell type. For example, when creating cell patterns of more than one cell type, current methods employ a two-step approach that uses complex masks to pattern cell-adhesive substrates via self-assembled monolayers or layers of certain proteins, followed by exposure of the desired cell type to the layers. In addition, such methods, while they can be utilized to form cellular arrays of more than one cell type, are still limited to fairly simple geometric patterns of cells.

As such, a need currently exists for a relatively inexpensive, quick, and efficient method of depositing arrays of viable cells onto a substrate.

SUMMARY OF THE INVENTION

In accordance with one embodiment of the present invention, a method for forming an array (e.g., two-dimensional or three-dimensional) of viable cells is disclosed. The method comprises ink-jet printing a cellular composition containing cells (e.g., eucaryotic, procaryotic, cell aggregates, etc.) onto a substrate. Multiple droplets of the cellular composition may be printed onto the substrate and allowed to fuse into a cohesive cellular assembly. Upon printing, at least about 25%, in some embodiments at least about 50%, in some embodiments at least about 75%, and in some embodiments, at least about 85% of the cells remain viable on the substrate after incubation for 24 hours at 37° C. in a 5% $CO_2$/95% $O_2$ environment. To facilitate the survival of the cells, a support compound may also be deposited onto the substrate. For example, in one embodiment, the support compound is a gel or a compound capable of forming a gel. For example, in one embodiment, a gel-forming compound is deposited onto the substrate and then formed into a gel by a variety of methods, such as thermal activation and/or crosslinking.

In accordance with another embodiment of the present invention, a method for forming an array of viable cells is disclosed that comprises supplying a cellular composition containing cells to at least one printer head of an ink-jet printer, the printer head defining an orifice through which the cellular composition is capable of flowing. One or more droplets are formed from the cellular composition, and the droplets are allowed to flow through the orifice so that the cells are printed onto the substrate. A support compound is also deposited onto the substrate for supporting the cells.

In accordance with still another embodiment of the present invention, an array is disclosed that is formed on a substrate from viable printed cells. A gel provides structural support for the cells, and the density of the cells when printed is from about 0.0001 to about 1 cell per square micrometer. If desired, the array may comprise cells of more than one cell type. In some embodiments, the density of the cells varies across at least a portion of the array.

In accordance with yet another embodiment of the present invention, an ink-jet printer is disclosed that is configured to deposit viable cells onto a substrate. The printer comprises a reservoir for containing the cells and a printer head in fluid communication with the reservoir. The printer head defines an orifice having a size of from about 2 to about 200 micrometers, and the cells are capable of flowing through the orifice without substantial clogging. The printer also comprises a pressurization actuator capable of facilitating the formation of a droplet containing the cells for flowing through the orifice. The pressurization actuator receives a voltage pulse that is sufficiently low to facilitate the survival of the cells. For example, in some embodiments, the voltage pulse ranges from about 1 to about 50 volts, and in some embodiments, from about 10 to about 20 volts. The pressurization actuator may be selected from the group consisting of piezoelectric crystals, acoustic devices, thermal devices, and combinations thereof. The printer head may be moveable in an −x direction. In addition, the printer may also comprise a feed mechanism for receiving the substrate, which may be configured to move the substrate in a −y direction.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which:

FIGS. 13A and 13B are photographs showing the results of mammalian cell printing in Example 2;

FIG. 14 is a top view of seven alternate layers of clear and tryan blue-dyed K-70 gel printed on a collagen-coated dish in Example 3;

Figure 1:
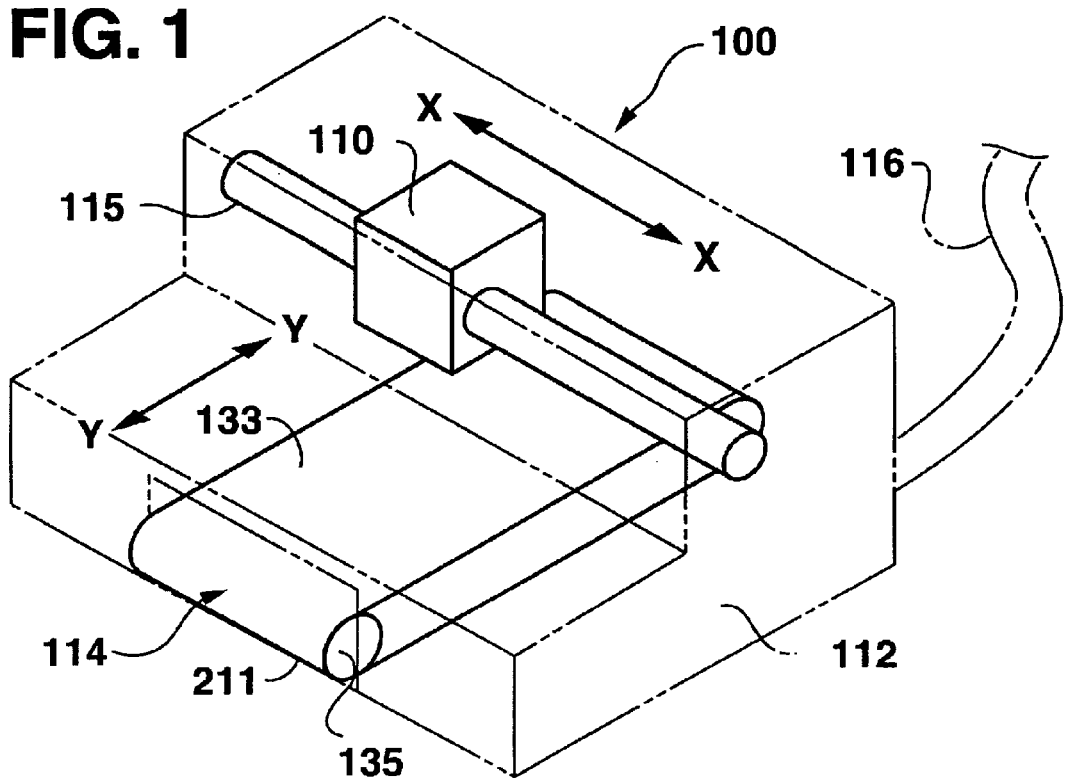
FIG. 1 is a schematic view of one embodiment of an ink-jet printer that may be used in the present invention.

Repeat use of reference characters in the present specification and drawings is intended to represent the same or analogous features or elements of the present invention.

DETAILED DESCRIPTION OF REPRESENTATIVE EMBODIMENTS

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

The present invention is generally directed to a method for ink-jet printing a cell composition onto a substrate. Specifically, the present inventors have discovered that arrays of cells may be formed according to the present invention that are not only viable, but are also printed in a controlled and predetermined manner onto a substrate. The ink-jet printing techniques of the present invention provide a variety of benefits over prior techniques for depositing arrays of cells onto a substrate. For instance, a multitude of small, individual drops of cells may be printed at a high density to allow fusing and ultimately the formation of cohesive cellular assemblies. In addition, because printing is conducted without contact, the likelihood of contamination is minimized.

Generally speaking, any known ink-jet printer and/or ink-jet printing system may be incorporated for use in the present invention. Ink-jet printers are typically either "DOD" (Drop-On-Demand) or "continuous" ink-jet printers. In a continuous ink-jet printer, a stream of fluid continuously issues from an orifice. A pressurization actuator (e.g., piezoelectric crystal, acoustic device, thermal device, etc.) induces pressure oscillations in the fluid stream and causes the stream to break into drops. For most DOD ink-jet printers, a pressurization actuator is used at each orifice to produce an ink-jet drop. Some examples of such DOD and continuous ink-jet printers are described in U.S. Pat. No. 4,646,106 to Howksins; U.S. Pat. No. 5,739,832 to Heinzl, et al.; U.S. Pat. No. 6,394,585 to Ross; U.S. Pat. No. 6,497,510 to Delametter, et al.; U.S. Pat. No. 6,527,378 to Rausch, et al.; U.S. Pat. No. 6,536,873 to Lee, et al.; U.S. Pat. No. 6,543,872 to Ohtsuka, et al.; U.S. Pat. No. 6,561,642 to Gonzalez; U.S. Pat. No. 6,536,895 to Kashiwagi, et al.; and U.S. Pat. No. 6,550,904 to Koitabashi, et al., which are incorporated herein in their entirety by reference thereto for all purposes. Commercially available examples of some suitable printers that may be adapted for use in the present invention are printers sold by Canon Inc., such as BJC-2100 or BJ-2200, and Hewlett-Packard Co., such as 550C or 660C.

In addition, various ink-jet printers used to print layers on plastic parts (known as "rapid prototyping") may also be adapted for use in the present invention. One example of such a printer is the ModelMaker II™ printer available from Solidscape, Inc. (formerly "Sanders-Prototype, Inc."). The ModelMaker II™ is designed to print onto jewelry, and is believed to utilize a wax mold that is infiltrated with a ceramic slurry to produce the desired part. A liquid-to-solid ink-jet printer deposits the polymer on a movable z-platform. Two molten polymers, such as a thermoplastic building wax and a supporting wax, are fed into heated movable ink-jet printer heads capable of motion in the x-y plane. The ink-jet heads deposit the materials as fine drops that solidify upon impact with a cooler mold surface. After the mold is built, the supporting wax is dissolved using an organic solvent that does not attack the building wax. Examples of such rapid prototyping printers are believed to be described in U.S. Pat. Nos. 5,040,911; 4,969,758; 4,948,280; 4,921,365; 4,896,980; 4,889,438; 4,772,141; 4,673,304; 4,594,597; 4,585,139; 4,291,992, which are incorporated herein in their entirety by reference thereto for all purposes.

Figure 2:
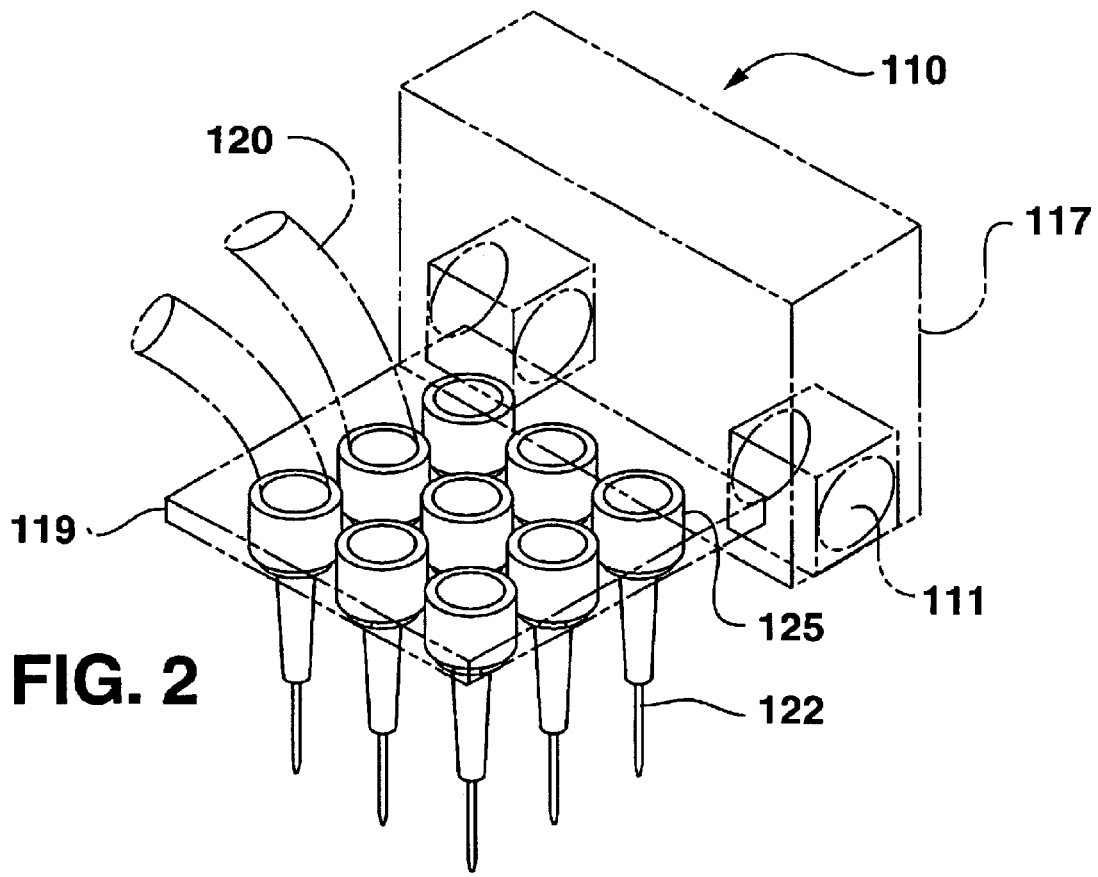
FIG. 2 is a schematic view of the printer head shown in FIG. 1.
Figure 3:
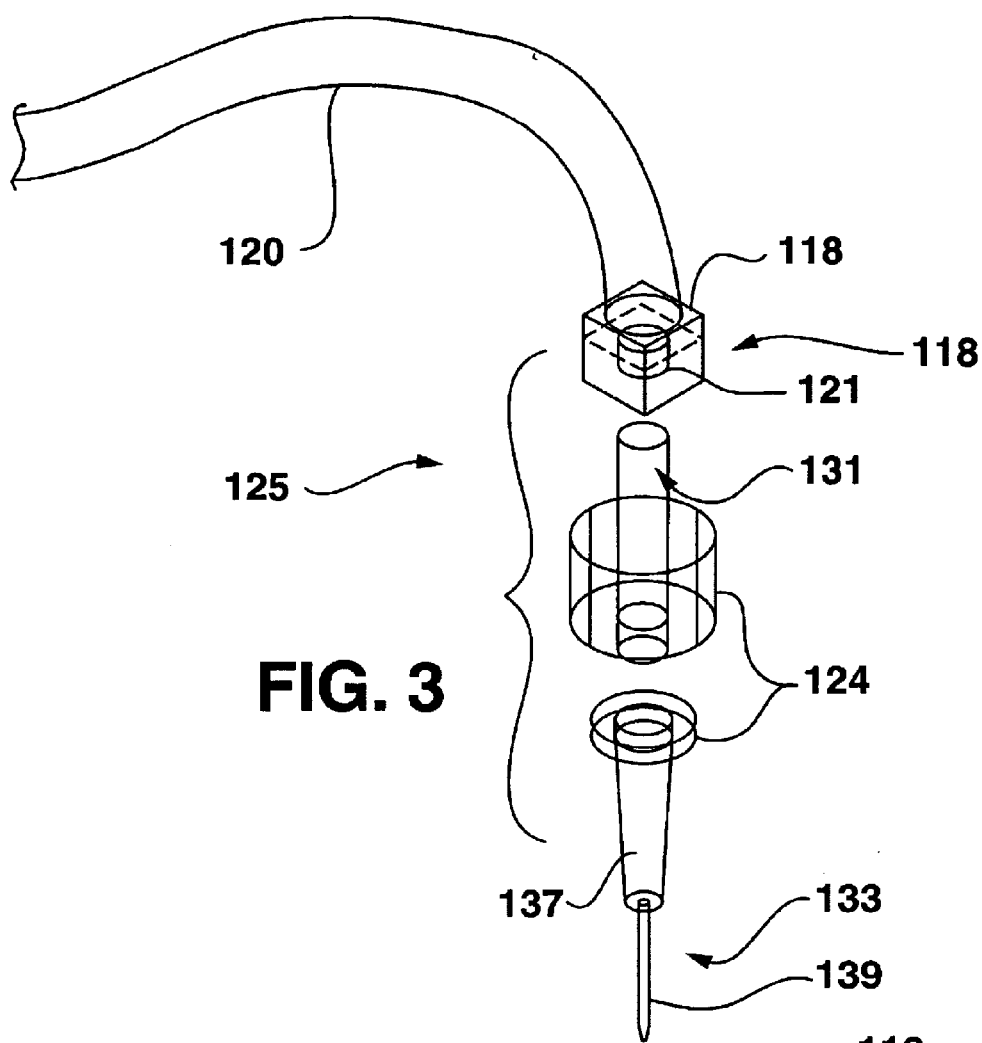
FIG. 3 is a schematic view of one of the nozzles shown in FIG. 2.

Referring to FIGS. 1–3, for example, one embodiment of a DOD ink-jet printer 100 that may be used in accordance with the present invention will now be described in more detail. The printer 100 includes a body 112 to which is connected a printer head 110. In one embodiment, the body 112 has a length of about 46 centimeters and a width of about 30.5 centimeters. The printer head 110 is moveably secured to a support member 115, which in one embodiment, has a length of about 41 centimeters and a diameter of about 1 centimeter. Specifically, in the illustrated embodiment, the printer head 110 includes openings 111 through which the support member 115 is inserted so that the head 110 remains moveable about the support member 115 in the −x direction. Alternatively, however, the printer head 110 may be stationary, or may be moveable in other directions.

The printer head 110 includes a support structure 117 to which is attached a deposition platform 119. In one embodiment, for instance, the support structure 117 has a length of about 4.5 centimeters and a width of about 4 centimeters, while the deposition platform 119 has a length of about 4.5 centimeters and a width of about 2 centimeters. One or more nozzles 125 are mounted to the platform for depositing a fluid onto a substrate. In this particular embodiment, the printer head 110 includes nine (9) independently operated nozzles 125. The fluid deposited from each nozzle 125 may be the same or different. For example, in one embodiment, different cell suspensions may be loaded into different nozzles 125 to form mixed cell arrays.

FIG. 3 is an exploded view of one of the nozzles 125 of the printer head 110. As shown, the nozzle 125 is attached to a connection member 120 that is in fluid communication with a remote reservoir (not shown) in which a fluid is stored. Alternatively, the reservoir may be contained within or near the printer head 110. For example, a conventional ink-jet cartridge may be used as a reservoir for a cell suspension. The connection member 120 allows the flow of a fluid between the reservoir and the nozzle 125. Desirably, the connection member 120 is flexible to allow the printer head 110 to move during the printing process. For instance, the connection member 120 may be formed from flexible tubing. The connection member 120 may also be in communication with more than one reservoir, if desired, such that multiple materials are mixed before and/or during the printing process. For example, in one embodiment, a cell suspension may be mixed with a cell nutrient prior to the printing process, with the resulting mixture being printed from a single nozzle 125.

As shown, the nozzle 125 includes a pressurization actuator 118. The pressurization actuator 118 may contain any device commonly used in ink-jet printers to form liquid drops. Examples of such actuators include, but are not limited to, piezoelectric crystals, acoustic devices, thermal devices, etc. In the illustrated embodiment, for instance, the actuator is a piezoelectric crystal. The pressurization actuator 118 receives a voltage pulse, and in response, induces pressure oscillations in a fluid received from a connection member 120. The magnitude of the voltage pulse may be selected to facilitate survival of cells in the fluid. For instance, in some embodiments, the voltage pulse ranges from about 1 to about 50 volts, in some embodiments, from about 5 to about 35 volts, and in some embodiments, from about 10 to about 20 volts. In one particular embodiment, the voltage pulse is about 15 volts. After formation, drops of the fluid are formed and travel through a gate 121.

Once a drop is formed, it may then be deposited onto the substrate through an orifice. The size and shape of the orifice may generally vary depending on the cell type, the desired printed pattern and density, and so forth. Generally, it is desired that the orifice is large enough to allow any particulates in a fluid to pass therethrough without substantial sticking or clogging, but small enough to provide the desired deposition accuracy. Thus, for instance, the orifice may be the same or greater diameter as compared to the size of cells in the fluid, such as from about 2 to about 200 micrometers. Moreover, the orifice may also be formed by an elongated channel that has a constant or variable diameter.

Referring again to FIG. 3, for example, an orifice having a variable diameter is shown as being defined by a central portion 131 and a deposition portion 133. The size and shape of the central portion 131 may generally vary to accommodate cells of different sizes. For example, in the illustrated embodiment, the central portion 131 has a cylindrical shape and a diameter of about 3 millimeters. In one embodiment, the deposition portion 133 is removably attached to the central portion 131 via a lock 124 (e.g., luer lock) as is generally known in the art. This allows independent removal of the deposition portion 133 from the remaining components of the nozzle 125 after use. Such a removable attachment may allow the same pressurization actuator 118 and/or central portion 131 to be used with various types of deposition portions, i.e., those having different shapes and/or sizes. Alternatively, the deposition portion 133 and central portion 131 are continuous and formed by a single structure.

In the illustrated embodiment, the deposition portion 133 includes a housing 137 into which a fluid flows. To facilitate deposition accuracy, the housing 137 may have a conical shape so the diameter of the housing 137 is about 4 millimeters at the top portion and about 2 millimeters at the bottom portion. From the housing 137, the fluid then flows to a hollow needle or tube 139. The size of the needle 139 depends on the type of fluid, the substrate, the printing pattern, and other factors. However, it is generally desired that the needle 139 is large enough to allow any particulates to pass therethrough without substantial sticking or clogging, but small enough to provide the desired deposition accuracy. For example, in one embodiment the needle 139 is a 30-gauge needle that allows cells up to about 100 micrometers in diameter to pass therethrough without substantial sticking or clogging. Of course, smaller and larger needles 139 are also contemplated in the present invention. For instance, in some embodiments, cells having diameters of up to several hundred micrometers (e.g., cell aggregates) may be printed in accordance with the present invention.

Figure 5:
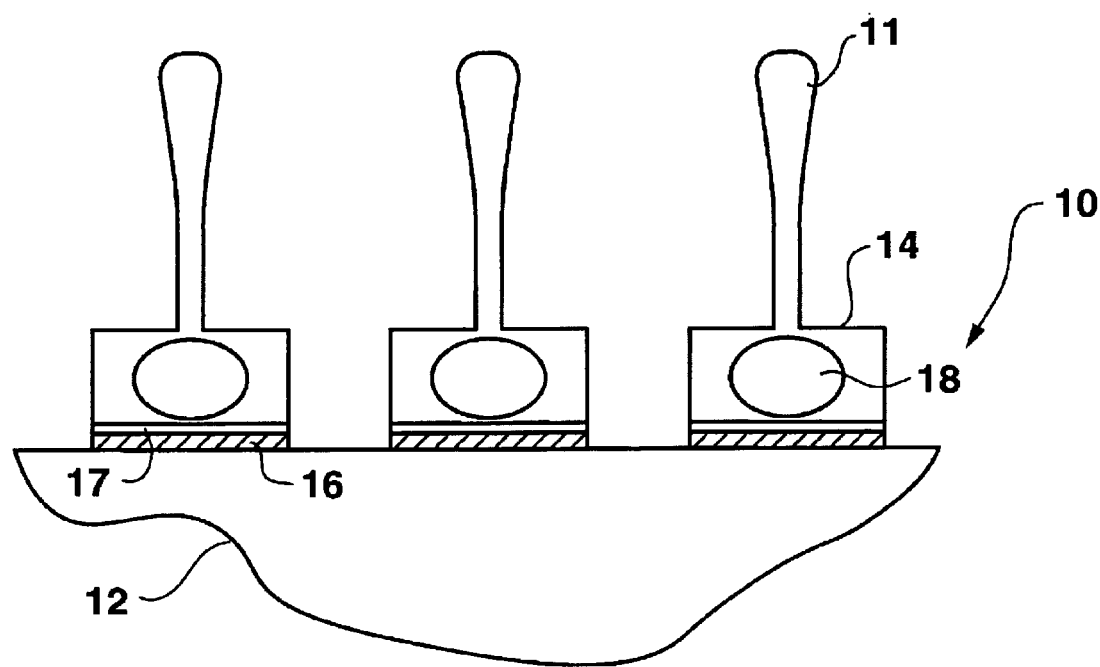
FIG. 5 is a schematic view of another embodiment of a printer head that may be used in the present invention.

Other printer heads are also contemplated in the present invention. For example, thermal ink-jet printer heads often use heater resistors disposed on a support member that are aligned with reservoirs and corresponding nozzles. These heater resistors are physically defined and electrically driven by conductive traces that can be photolithographically formed on the surface of a suitable resistor layer material, such as tantalum-aluminum. The heater resistors are typically isolated from the overlying reservoirs by dielectric materials, such as silicon carbide and silicon nitride. Referring to FIG. 5, one embodiment of such a printer head is illustrated. As shown, the printer head 10 includes a support member 12, such as silicon, that supports a number of reservoirs 14 configured to receive a fluid 11. Heaters or resistors 16 are disposed within the reservoirs 14, and passavation layers 17 are formed over the resistors 16 that contain a dielectric material. To expel a jet of the fluid 11, the heaters or resistors 16 are heated rapidly to cause vapor bubbles 18 to form within the reservoirs 14. The vapor bubbles 18 cause a quantity of a fluid 11 to be ejected onto a substrate.

Referring again to FIG. 1, the printer 100 may also contain a feed mechanism 114 to receive a substrate. For example, in the illustrated embodiment, the feed mechanism 114 is a conveyor belt feed roller that includes a carrier surface 133 for receiving a substrate and wheels 135 that rotate in a counter and/or counterclockwise direction for moving the substrate in the −y direction. In one embodiment, for instance, the feed mechanism may utilize rubber wheels and a glass carrier surface. In another embodiment, the carrier surface may be formed from a plastic or rubber material. Other well-known feed mechanisms may also be used in the present invention, such as timing belts, etc. In addition, the feed mechanism 114 may also move the substrate in others directions, including the −x direction, as well as in a circuitous route.

Besides the components discussed above, it should be understood that other well-known components of ink-jet printers may also be utilized in the present invention. For example, the printer 100 may include a bus 116, as well as a variety of other standard printer components, e.g., logic board, encoder, etc., that are not specifically shown, but are generally known in the art. In addition, the printer 100 may also contain a height-adjustable support member (not shown) on which the printer head 110, support member 115, and an encoder assembly (not shown) are mounted. The height-adjustable support member (e.g., screws, etc.) may, for instance, allow the distance between the printer head 110 and the substrate to be adjusted and controlled. This may be particularly useful for substrates having a relatively large thickness, such as a Petri dish containing a layer of agar or collagen. The ability to adjust the height of the printer head 110 may also enhance the ability to precisely control the distance that the cell composition falls from the nozzle 125 to the surface of the substrate. Minimizing this distance may further facilitate the survival of cells after printing and enhance precision. For example, the distance from the exit of the nozzle 125 to the surface of the substrate is typically from about 0.1 to about 50 millimeters, in some embodiments, from about 0.5 to about 20 millimeters, and in some embodiments, from about 0.5 to about 3 millimeters.

Various types of cells may be printed according to the present invention. For example, both procaryotic and eucaryotic cells may be printed. Procaryotes are cells having no nucleus or only a primitive nucleus, including both bacterial and cyanobacteria, such as, *E. coli*, algae, and so forth. On the other hand, eucaryotes are cells having a defined nucleus, such as fungi, protozoa, mammalian cells (e.g., bovine aortal endothelial cells ("BAEC"), Chinese hamster ovary cells ("CHO"), smooth muscle cells ("SMC"), etc.), and so forth. Procaryotes typically have a cell diameter of from about 2 to about 10 micrometers, while eucaryotes typically have a cell diameter of from about 10 to about 200 micrometers. Most bacteria cells, for instance, have a cell diameter of about 2 micrometers, while most mammalian cells have a cell diameter of from about 15 to about 200 micrometers.

In one embodiment, cells may be printed according to the present invention in the form of "cell aggregates", which are clumps of cells adhered to each other. Cell aggregates may be made of a single cell type or multiple cell types, such as CHO aggregates or BAEC/SMC aggregates. Cell aggregates typically have a diameter that ranges from about 100 micrometers to about 3 millimeters.

Although not required, cells can typically be printed in the form of a "cell composition" that contains a liquid carrier for the cells. The cell composition can be in the form of a suspension, solution, or any suitable form. Examples of suitable liquid carriers include, but are not limited to, water, ionic buffer solutions (e.g., phosphate buffer solution, citrate buffer solution, etc.), liquid media (e.g., modified Eagle's medium ("MEM"), Hanks' Balanced Salts, etc.), and so forth. For instance, the use of a liquid carrier in the cell composition can ensure adequate hydration and minimize evaporation of the cells after printing. However, the probability of obtaining viable cells in any given printed drop also decreases with decreasing cell concentration. Thus, it is typically desired that the concentration of cells within a given drop vary from about 1 cell to about $5 \times 10^7$ cells per drop, in some embodiments from about 1 cell to about $5 \times 10^5$ cells per drop, and in some embodiments, from about 1 cell to about $2.5 \times 10^3$ cells per drop. Likewise, the concentration of cells in the cell composition typically varies from about $1 \times 10^3$ to about $1 \times 10^{16}$ cells per milliliter, in some embodiments, from about $1.5 \times 10^5$ to about $5 \times 10^{14}$ cells per milliliter, and in some embodiments, from about $3 \times 10^5$ to about $1 \times 10^9$ cells per milliliter.

Cell compositions may be printed according to the present invention on a variety of different types of substrates. Examples of some suitable substrate materials include, but are not limited to, glass, quartz, papers, plastics, gels, scaffolds, membranes, etc.

Various mechanisms may be employed to facilitate the survival of the cells during and/or after printing. Specifically, compounds may be utilized that "support" the printed cells by providing hydration, nutrients, and/or structural support. These compounds may be applied to the substrate using conventional techniques, such as manually, in a wash or bath, through vapor deposition (e.g., physical or chemical vapor deposition), etc. These compounds may also be combined with the cell composition before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the printer head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc. One example of a collagen gel for facilitating cell growth is described in *Collagen As a Substrate for Cell Growth and Differentiation*, Methods in Enzymology, Strom and Michalopoulous, Vol. 82. 544–555 (1982).

There are several mechanisms, for instance, that can lead to formation of a hydrogel. For instance, temperature change ("thermogelling"), pH change, cross-linking, and/or solvent exchange can lead to the formation of the gel. Thus, for example, a hydrogel may be activated after printing by lowering its temperature, such as lowering the temperature to about 37° C. (i.e., body temperature) or below, and in some embodiments, to about 25° C. or below (i.e., room temperature). One example of such a thermogelling hydrogel polymer is a random copolymer of a [meth]-acrylamide derivative and a hydrophilic comonomer, wherein the random copolymer is in the form of a plurality of linear chains having a plurality of molecular weights greater than or equal to a minimum gelling molecular weight cutoff. The [meth]-acrylamide derivative is an N,N'-alkyl substituted [meth]-acrylamide including, but not limited to, N-isopropyl[meth]-acrylamide, N,N'-diethyl[meth]-acrylamide, N-[meth]-acryloylpyrrolidine, N-ethyl[meth]-acrylamide, and combinations thereof. The hydrophilic comonomer is any hydrophilic comonomer that co-polymerizes with the [meth]-acrylamide derivative. Preferred hydrophilic comonomers are hydrophilic [meth]-acryl-compounds including, but not limited to, carboxylic acids, [meth]-acrylamide, hydrophilic [meth]-acrylamide derivatives, hydrophilic [meth]-acrylic acid esters. The carboxylic acid may be, for example, acrylic acid, methacrylic acid and combinations thereof. The hydrophilic acrylamide derivatives include, but are not limited to, N,N-diethyl[meth]-acrylamide, 2-[N,N-dimethylamino]ethyl[meth]-acrylamide, 2-[N,N-diethylamino]ethyl[meth]-acrylamide, or combinations thereof. The hydrophilic [meth]-acrylic esters include, but are not limited to, 2-[N,N-diethylamino]ethyl[meth]-acrylate, 2-[N,N-dimethylamino]ethyl[meth]-acrylate, and combinations thereof. Such thermogelling polymers are believed to be described in more detail in U.S. Pat. No. 6,103,528 to An, et al., which is incorporated herein in its entirety by reference thereto for all purposes.

The thermogelling hydrogel polymers may also be biodegradable. For example, one such thermogelling, biodegradable polymer contains a polyethylene glycol (PEG) block linked to a biodegradable polyester block. The polymer may have a general formula of $A_n(B)$, where n is greater than 2, A is selected from a polyethylene glycol block and a biodegradable polyester block, B is selected from the group consisting of a polyethylene glycol block and a biodegradable polyester block, and A is different from B, and an aqueous solution. The biodegradable polyester block is preferably poly(DL-lactic acid), poly(L-lactic acid), poly(glycolic acid), poly($\epsilon$-caprolactone), poly($\gamma$-butyrolactone), poly($\alpha$-valerolactone), poly($\beta$-hydroxybutyric acid), and their copolymers or terpolymers. The copolymers and/or terpolymers may also be selected from poly(DL-lactic acid-co-glycolic acid), poly(L-lactic acid-co-glycolic acid), poly($\epsilon$-caprolactone-co-DL-lactic acid), and copoly($\epsilon$-caprolactone-co-DL-lactic acid-glycolic acid). The biodegradable polyester blocks may have a maximum molecular weight of about 100,000, in some embodiments from about 1,000 to about 30,000, and in some embodiments, from about 1,000 to about 10,000. The polyethylene glycol (PEG) block may have an average molecular weight of from about 300 to about 20,000, and in some embodiments, from about 500 to about 10,000. Such biodegradable thermogelling polymers are believed to be described in more detail in U.S. Patent Application Publication No. 2002/0173586 to Jeong, et al., which is incorporated herein in its entirety by reference thereto for all purposes.

Other exemplary thermogelling polymers include poly[N-isopropylacrylamide-co-2-(N,N-dimethylamino)-ethyl acrylate] copolymers, such as those developed by Gutowska, Jeong, and Jasionowski ("Injectable Gels for Tissue Engineering", Anat. Rec., 2001, 263:342–349). Moreover, still other suitable thermogelling polymers are believed to be described in U.S. Pat. No. 5,492,937 to Bogentoft, et al. and U.S. Pat. No. 5,702,717 to Cha, et al., which are incorporated herein in their entirety by reference thereto for all purposes. In addition, suitable pH/thermosensitive biodegradable hydrogels are believed to be described in U.S. Pat. No. 6,451,346 to Shah, et al., which is incorporated herein in its entirety by reference thereto for all purposes.

As indicated above, other types of gels may also be used in the present invention. For instance, in one embodiment, a crosslinked hydrogel may be utilized as a support compound. Any of a variety of known crosslinking techniques may be utilized, such as chemical crosslinking, irradiation crosslinking (e.g., electron beam), and so forth. In most embodiments, chemical crosslinking using a crosslinking agent is particularly desired. Some examples of suitable crosslinkable hydrogel polymers are believed to include, but are not limited to, hyaluronic acid, alginic acid, carrageenan, chondroitin sulfate, dextran sulfate, pectin, chitosan, polylysine, collagen, alginate, carboxyethyl chitin, fibrin, poly(ethylene glycol-lactic acid-ethylene glycol), poly(lactic acid-ethylene glycol-lactic acid), poly(lactic glycolic acid-ethylene glycol-lactic glycolic acid, poly(hydroxy butyrate), poly(propylene fumarate-co-ethylene glycol), poly(ethylene glycol-butylene oxide-terephtalate), poly(methylmethacrylate-co-hyroxyethylmethacrylate, poly(ethylene glycol-bis-(lactic acid-acrylate), poly(ethylene glycol-g-(acrylamide-co-vamine)), polyethylene glycol+/–cyclodextrins, polyacrylamide, poly(N-isopropyl acrylamide-co-acetic acid), poly(N-isopropyl acrylamide-co-ethylmethacrylate), poly(vinylacetate/vinylalcohol), poly(N-vinyl pyrrolidone), poly(biscarboxy-phenoxy-phospazene), poly(acrylonitrile-co-allyl sulfonate), poly(ethylene glycol dimethacrylate-sulfate), poly(ethylene glycol-co-peptides), alginate-g-poly(ethylene oxide-propylene oxide-ethylene oxide), chitosan-g-poly(ethylene oxide-propylene oxide-ethylene oxide), poly(lactic glycolic acid-c-serine), poly(hydoxypropylacrylamide-g-peptide), poly(hydroxyethylmethacrylate/Matrigel), hyaluronic acid-g-N-isopropyl polyacrylamide, collagen-acrylate, and alginate-acrylate. Crosslinking agents for polymers, such as described above, may include, but are not limited to, magnesium chloride, calcium chloride, cationic polymers, anionic polymers, buffering salts, glutaraldehyde, ethylene glycol dimethacrylate, diisocyanate, and so forth.

Besides gels, other support compounds may also be utilized in the present invention. Extracellular matrix analogs, for example, may be combined with support gels to optimize or functionalize the gel. One or more growth factors may also be introduced to the printed cell arrays. For example, slow release microspheres that contain one or more growth factors in various concentrations and sequences may be combined with the cell composition to accelerate and direct the cell fusion process. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways could be included in cell aggregates to be printed according to the invention. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following printing of a layer. In addition, adhesives, such as arginine-glycine-aspartic acid ligands, may enhance the adhesion of cells to a gelling polymer or other support compound. In addition, extracellular proteins, extracellular protein analogs, etc., may also be utilized.

Figure 4:
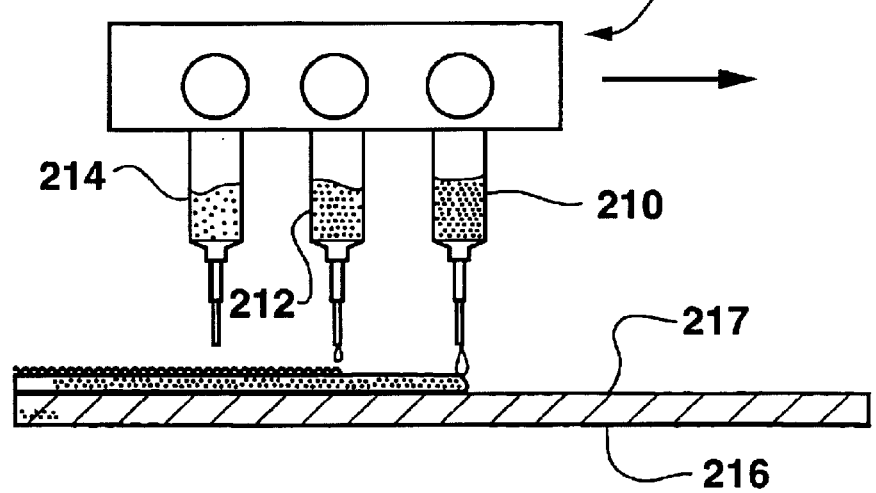
FIG. 4 is a schematic view of one embodiment of the present invention for depositing viable cells onto a substrate.

The manner in which the support compound and/or cells may be deposited onto a substrate may generally vary. For instance, FIG. 4 is a schematic illustration of one embodiment in which layers are deposited onto a substrate 216 using the printer 100 of FIG. 1. Initially, the substrate 216 is supplied at an end 211 of the feed mechanism 114 (FIG. 1). The wheels 135 of the feed mechanism 114 rotate clockwise, so that the substrate 216 is moved closer to the printer head 110. After reaching the desired position, the wheels 135 stop so that the printer head 110 is positioned to deposit the fluids at the desired location. In this embodiment, three fluids (the same or different) are supplied from reservoir(s) (not shown) to nozzles 210, 212, and 214 of the printer head 110. The printer head 110 may make multiple passes over the substrate 216. For instance, in one embodiment, the printer head 110 moves back and forth in the –x direction to make multiple passes over the substrate 216 as it rests on the feed mechanism 114. A single layer or multiple layers may then be printed onto a surface 217 of the substrate 216 without removing the substrate 216 from the printer 100.

In one embodiment, for instance, the fluid from nozzle 210 includes a cellular suspension, the fluid from nozzle 212 includes a hydrogel polymer solution, and the fluid from nozzle 214 includes a crosslinking agent for the hydrogel polymer. When the crosslinking agent supplied from the nozzle 214 contacts the hydrogel polymer from the nozzle 212, a layer of crosslinked hydrogel may form on the substrate 216. Alternatively, the hydrogel polymer and/or the crosslinking agent may be initially mixed with the cellular suspension prior to deposition from the nozzle 212. Depending on the manner in which the hydrogel polymer and/or crosslinking agent are deposited, as well as the characteristics of the different fluids (viscosity, temperature, etc.), more or less mixing of the fluids may occur prior to the formation of the hydrogel. In some cases, the characteristics of the fluids are such that little mixing occurs between the hydrogel and cellular suspension prior to formation of the crosslinked gel. In this instance, the printed hydrogel forms a distinct layer over the cellular layer. However, when the hydrogel polymer is able to mix with the cellular suspension before crosslinking, it can flow within and around the individual cells or cell aggregates in the suspension before being structurally hardened.

Figure 20:
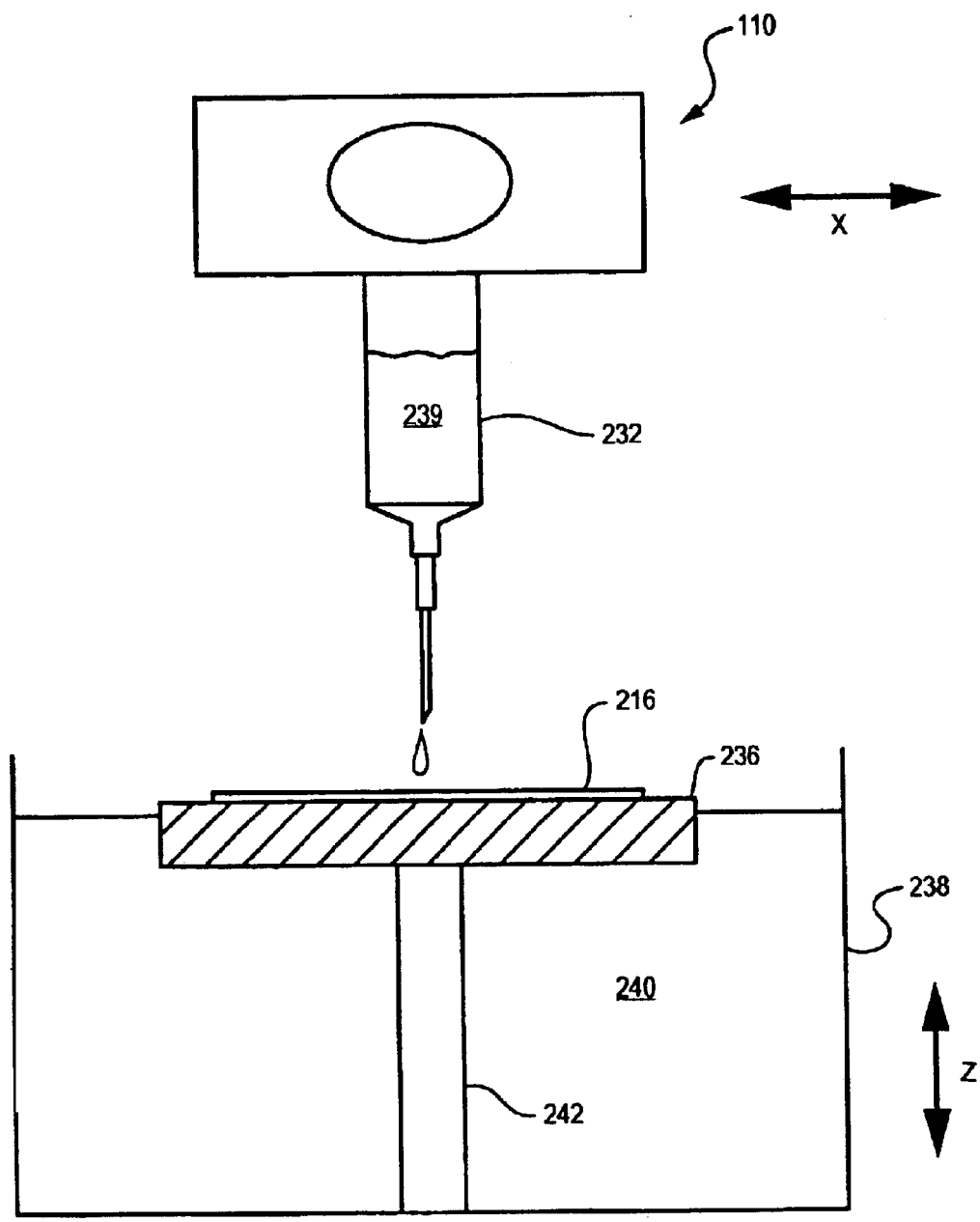
FIG. 20 is a schematic view of a printer head that may be used in one embodiment of the present invention.

FIG. 20 depicts an alternative embodiment of the present invention for depositing layers onto a substrate 216 using the printer 100 of FIG. 1. According to this method, a stage 236 holds the substrate 216 below the printer head 110. The printer head 110 moves in the −x direction and optionally in the −y direction to deposit a composition 239 onto the substrate 216 from a nozzle 232. The stage 236 is mounted on a shaft 242 that moves of stage 236 in the −z direction within a chamber 238. If desired, the stage 236 may be connected to a feeder mechanism of the printer (not shown) to allow movement of the stage 236 in the −y direction. Regardless, the chamber 238 is filled with a solution 240 that may, for instance, contain a support compound. In some embodiments, a fluid 239 is first printed onto a surface of the substrate 216. Thereafter, the stage 236 is lowered into the solution 240, which includes nutrients and/or hydration additives. Optionally, a hydrogel polymer and/or crosslinking agent may be included within the fluid 239 and/or contained within the chamber 238. Thus, for instance, the fluid 239 may include a cellular suspension and crosslinking agent that are printed onto the substrate 216 via nozzle 232. The stage 236 is then lowered into the solution 240 so that the upper surface of the substrate 216 is positioned a certain distance below the surface of the solution 240 that is at least equal to or greater than the average diameter of the cells applied to the substrate 216. For instance, the substrate 234 may be immersed at least about 10 microns, in some embodiments from about 50 microns to about 1 millimeter, and in some embodiments, from about 100 to about 500 microns (e.g., about 200 microns) within the solution 240. The crosslinking agent will react with the hydrogel polymer to form a chemically crosslinked hydrogel, and the cells in the fluid 239 may be trapped in the developing hydrogel and provide a supportive structure for the living, developing cells. Additional layers of cells may be built up by simply repeating the process.

Figure 6:
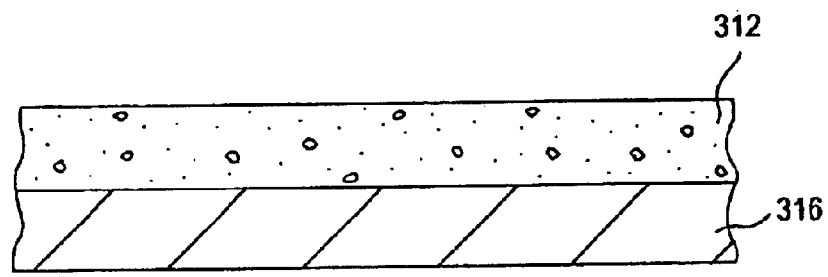
FIG. 6 is a schematic view of one embodiment of a substrate printed with a single layer in accordance with the present invention.

The printing techniques of the present invention may be utilized to form various types of arrays on a substrate. Two-dimensional arrays may be formed by printing a single layer of a cell composition onto a substrate. For instance, FIG. 6 illustrates a two-dimensional array in which a single layer 312 is present on a substrate 316. The single layer 312 may contain cells optionally mixed with a support compound, such as a thermogelling polymer. Two-dimensional arrays are particularly useful when depositing procaryotic cells (e.g., bacteria) onto a substrate.

Figure 7:
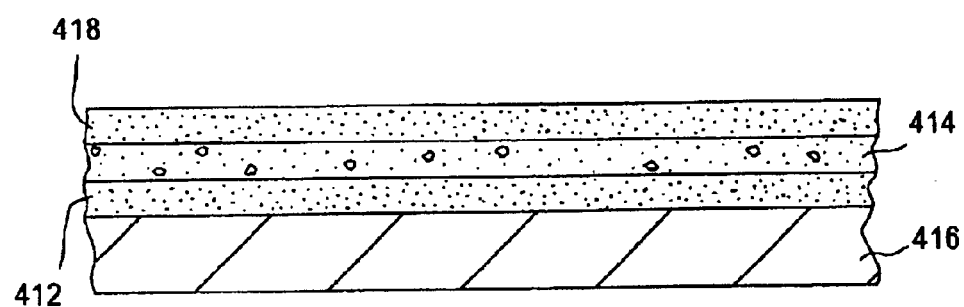
FIG. 7 is a schematic view of one embodiment of a substrate printed with three layers in accordance with the present invention.

Besides two-dimensional arrays, three-dimensional arrays may also be formed. Three-dimensional cell arrays are commonly used in tissue engineering and biotechnology for in-vitro and in-vivo cell culturing. In general, a three-dimensional array is one which includes two or more layers separately applied to a substrate, with subsequent layers applied to the top surface of previous layers. The layers can, in one embodiment, fuse or otherwise combine following application or, alternatively, remain substantially separate and divided following application to the substrate. Three-dimensional arrays may be formed in a variety of ways in accordance with the present invention. For example, in one embodiment, three-dimensional arrays may be formed by printing multiple layers onto the substrate. Referring to FIG. 7, for instance, one embodiment of a multi-layered, three-dimensional array is illustrated. In this particular embodiment, successive layers of a three-dimensional array are generated by printing a support layer 412 onto the substrate 416, printing a cell layer 414 on the support layer 412, printing another support layer 418 on the cell layer 414, and repeating this process until the desired number of layers are achieved. Such layers may be printed according to the methods illustrated in FIG. 4 or 20. For instance, the nozzle 210 may deposit the support layer 412, the nozzle 212 may deposit the cell layer 414, and the nozzle 214 may deposit the support layer 418. Such a sequential printing technique provides a relatively effective and inexpensive method for forming complex three-dimensional cellular arrays within a supporting structure.

The thickness of a printed layer (e.g., cell layer, support layer, etc.) may generally vary depending on the desired application. For example, in some embodiments, the thickness of a layer containing cells is from about 2 micrometers to about 3 millimeters, and in some embodiments, from about 20 micrometers to about 100 micrometers. Further, as indicated above, support compounds, such as gels, are often used to facilitate the survival of printed cells. The present inventors have discovered that the development of a cellular assembly may be increased when the thickness of the support layer(s) (e.g., between cells) is approximately the same as the size of the cells deposited adjacent to the support compound.

When printing certain types of two-dimensional or three-dimensional arrays, it is sometimes desired that any subsequent cell growth is substantially limited to a predefined region. Thus, to inhibit cell growth outside of this predefined region, compounds may be printed or otherwise applied to the substrate that inhibit cell growth and thus form a boundary for the printed pattern. Some examples of suitable compounds for this purpose include, but are not limited to, agarose, poly(isopropyl N-polyacrylamide) gels, and so forth. In one embodiment, for instance, this "boundary technique" may be employed to form a multi-layered, three-dimensional tube of cells, such as blood vessels. For example, a cell suspension may be mixed with a first gel ("Gel A") in one nozzle, while a second gel ("Gel B") is loaded into another nozzle. Gel A induces cell attachment and growth, while Gel B inhibits cell growth. To form a tube, Gel A and the cell suspension are printed in a circular pattern with a diameter and width corresponding to the diameter and wall thickness of the tube, e.g., from about 3 to about 10 millimeters in diameter and from about 0.5 to about 3 millimeters in wall thickness. The inner and outer patterns are lined by Gel B defining the borders of the cell growth. For example, a syringe containing Gel A and "CHO" cells and a syringe containing Gel B may be connected to the nozzle. Gel B is printed first and allowed to cool for about 1 to 5 minutes. Gel A and CHO cells are then printed on the agarose substrate. This process may be repeated for each layer.

In one embodiment, Gel A is formed from: (1) 3.33 milligrams per milliliter collagen dissolved in 0.0174 M acetic acid, (2) 2× serum-free Dulbecco's Modified Eagle's Media, and (3) 0.34 N NaOH solution. Solution (1) may be formed by diluting glacial acetic acid with triply distilled water. This solution is mixed and filter sterilized. Lyophilized Type I collagen is dissolved in this solution for a final concentration of 3.33 milligrams per milliliter. The dissolving process is carried out in an ice bath (T<4° C.) for 48 hours with periodic agitation for mixing. The collagen is recognized by the cells for binding and the gel structure maintains cell placement and tissue shape. Solution (2) may be formed by dissolving Powdered DMEM (Sigma D-7777) in 495 milliliters of triply distilled water. 5 milliliters of 100× antibiotic antimycotic solution (Sigma A-9909) and 1.5 grams of sodium bicarbonate are added to the mixing solution. The solution is thoroughly stirred and then filter sterilized. This solution fortifies the gel with nutrients for the cells and contains a pH-indicating dye to allow for visual pH monitoring. Finally, solution (3) may be formed by dissolving solid NaOH in water. The solution is filter sterilized and used for neutralization of the collagen gel. The gel may be formed by mixing solutions (1)–(3) in a ratio of 17:2.66:0.51, respectively (i.e., 1 ml collagen solution:156.6 ml 2×DMEM:30 ml 0.34M NaOH). The mixture is maintained at 4° C. Moreover, in one embodiment, Gel B is formed by adding 1 gm of agarose to 100 milliliters of water and shaking for 5 seconds. The mixture is then heated to about 80° C. for about 15 minutes to achieve a clear liquid. The mixture is then connected to a nozzle that is maintained at about 80° C. so that gel formation only occurs when the mixture is cooled to room temperature.

In addition to layer-by-layer printing techniques, three-dimensional arrays may also be formed by printing only a single layer of cells onto a substrate. In such embodiments, the layer of cells may be allowed to grow and develop into a multi-layered structure. Cell aggregates may be particularly useful in forming three-dimensional arrays in this manner. As is generally known in the art, the fusion of cell aggregates is a spontaneous phenomenon in an aggregate suspension. Both cell-to-substrate and cell-to-cell fusion forces exist in such cell suspensions when deposited on a substrate. If the cell-to-substrate forces are greater than the cell-to-cell forces, a two-dimensional cellular assembly may develop. However, if the cell-to-cell forces are greater, a three-dimensional cellular assembly may develop. Thus, in certain embodiments, such as when a three-dimensional cellular assembly is desired, for example, the use of cell aggregates can overcome the cell-to-substrate fusion forces and a three-dimensional cellular assembly can be developed.

Regardless of whether the printed array is two- or three-dimensional, it has been surprisingly discovered that a substantial portion of cells printed according to the present invention remain viable, i.e., metabolically active, on the substrate after printing. For example, in some embodiments at least about 25%, in some embodiments at least about 50%, in some embodiments at least about 75%, and in some embodiments, at least about 85% of the printed cells can remain viable on the substrate after incubation for 24 hours at 37° C. in a 5% $CO_2$/95% $O_2$ environment, as determined by an appropriate Live/Dead assay, such as those commercially available from Molecular Probes Inc. This may be accomplished despite the fact that the cell composition is subjected to relatively harsh conditions during the formation of drops by the pressurization actuator, i.e., shear forces up to about 10 meters per second, and in some instances, temperatures of up to about 300° C. Without intending to be limited by theory, it is believed that the relative high cell survival rate achieved according to the present invention is a result of a variety of factors. For example, it is believed that only a limited amount of heat is transferred to the cell composition due to the speed of the deposition process and the resulting short amount of time required for deposition. Specifically, the ink-jet based system of the present invention may deposit up to about 50,000 drops per minute, while the speed of conventional cell deposition systems is only about 100,000 drops per hour. The limited heat transfer thus causes only a small temperature increase in the composition and little or no damage to the cells.

Using the techniques described above, it has been discovered that cells may be printed onto a substrate and remain viable. However, not only does the present invention provide a mechanism for ensuring cell survival, it also provides the ability to easily, quickly, and inexpensively manipulate the types of patterns, densities, etc., that may be printed. For instance, the printed patterns may be simple or complex, and have a shape that is regular or irregular. In fact, due to the control provided by the present invention, there is essentially no limit on the patterns or shapes capable of being printed according to the present invention.

Furthermore, the printed density may also be selectively varied to attain the desired results. The desired density generally depends on a variety of factors, such as the nature of the cells, the type of substrate, and the ultimate application for which the cells are intended. In some embodiments, the printed cells are relatively spaced apart (i.e., low cell density), with each drop of cells being allowed to grow and develop separately. In such cases, the cell density may range from about 0.1 to about 2 cells per square millimeter, and in some embodiments, from about 0.25 to about 1 cell per square millimeter. In other embodiments, the printed cells are in relative close proximity (i.e., high cell density) to facilitate fusion of adjacent cells and development of a cohesive cell assembly. In such cases, the cell density may range from about 0.0001 to about 1 cell per square micrometer, and in some embodiments, from about 0.0004 to about 0.25 cells per square micrometer. In fact, it has been discovered that the present invention may actually allow the deposition of higher cell densities than previously realized using conventional techniques. In one embodiment, for example, a colony of bacteria (approximately 2 micrometers in diameter) may be printed according to the present invention onto a substrate at a cell density of about 100 drops per square centimeter. Thus, a substrate of about 22 centimeters×22 centimeters can have about 48,400 cell drops printed in a single layer. In contrast, a similar bacteria colony array deposited by conventional methods will generally have only about 3,456 bacteria on a 8 centimeter×12 centimeter membrane filter, far fewer than can be attained using the present invention.

To achieve the desired printed cell density, a variety of parameters may be adjusted. For instance, cell density is dependent on the concentration of the cells in the cell compositions. Specifically, for cells of the same size, smaller cell concentrations generally produce lower cell densities, while higher cell concentrations generally produce higher cell densities. However, if the cell concentration is too high, the likelihood of inadequate hydration is increased. Thus, to balance these concerns, it is often desired to provide the cell composition with higher cell concentrations (e.g., $1\times10^{10}$ cells per milliliter) when printing higher cell densities. Cell density is also dependent on the size of the drops that are delivered from the printer head, which in turn, depends on the size of the cells. Specifically, at a constant concentration, larger cells generally produce lower cell densities than smaller cells. Thus, when it is desired to print larger cells at high densities, the cell concentration may be selectively adjusted as needed (e.g., increased).

Regardless of the pattern and/or density selected, the present invention may utilize various control techniques to ensure that the desired results are achieved. Unlike conventional techniques for printing cells that involve contact-deposition, the present invention provides a precise, well-controlled method of printing that does not substantially risk contamination. The non-contact, ink-jet printing techniques employed in the present invention also allow for better control than previously realized when depositing viable cells onto a substrate. Generally speaking, any well-known ink-jet printing control technique may be utilized in the present invention. For instance, a printer driver may be used to control the movement of the printer head, the movement of the substrate, the voltage delivery to the printer head, etc. Some suitable ink-jet printing control techniques that may be adapted for use in the present invention are described in U.S. Pat. No. 6,543,872 to Ohtsuka, et al. and U.S. Pat. No. 6,550,904 to Koitabashi, et al.

Figure 8:
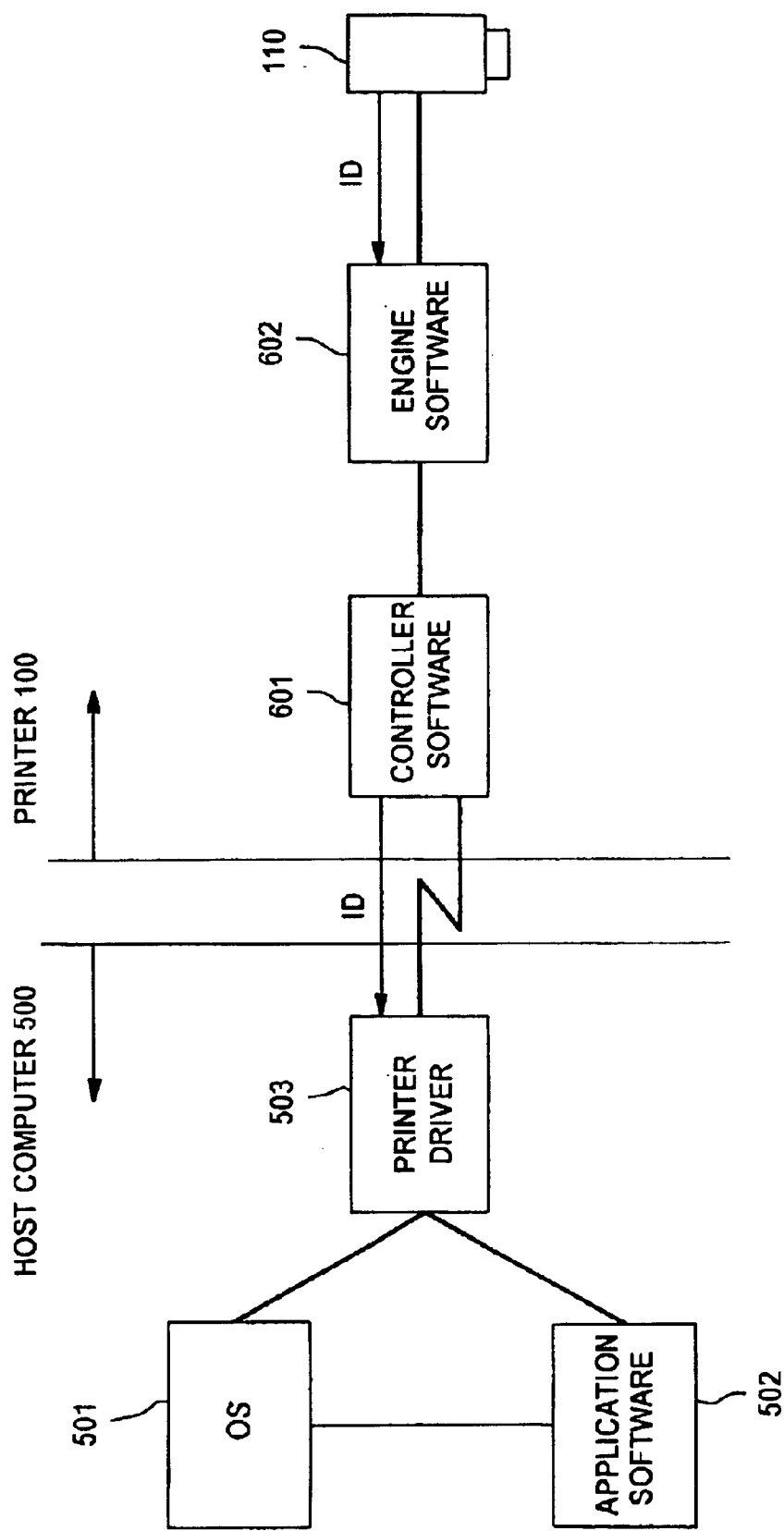
FIG. 8 is a block diagram of one embodiment of a control system that may be used in the present invention.

Referring to FIG. 8, for instance, a block diagram of one embodiment of a control system that may be used in the present invention is shown. As shown, the system includes a host computer 500 and an ink-jet printer 100 (FIG. 1). In the host computer 500, the exchange of various data and control are generally performed between an OS (Operating System) 501 and application software 502 that operates on the OS 501. Print data is exchanged between the OS 501, the application software 502, and a printer driver 503, and is sent to the printer 110 through the printer driver 503. The present invention is by no means limited to any particular printer driver because, as is well known to those skilled in the art, numerous types of printer drivers may accomplish the same functions desired in the present invention.

The flow of data in the process of printing out cell composition(s) from the printer 100 is generally described below. Typically, a user first inputs the desired cell density and pattern into the application software 502. These data signals are then sent to the printer driver 503. The printer driver 503 performs processing for the received signals, and also generally converts them into binary signals. The printer driver 503 sends these signals to the interface, in the host computer 500, which is used for the printer 100 or the interface for a file storage unit or the like. The signals are then sent as output to the interface for the printer 100, and the data signals are sent to controller software 601 in the printer 100. Matching between the set print mode and a printer head 110 is checked. Thereafter, the print data is transferred to engine software 602. In this case, the engine software 602 interprets the received data as data indicating the print mode and the data structure designated by the controller software 601, converts the print data into discharge pulses, and sends them to the printer head 110. With this operation, cell composition(s) are discharged from the printer head 110. The ID information of the printer head 110, the ID information of each cell composition reservoir, etc., are sent to the engine software 602. On the basis of these pieces of information about the printer head 110, the engine software 602 assigns print buffers for storing print data of the respective compositions, and optimizes various settings. The pieces of information are further sent to the host computer 500 and used as pieces of information for, for example, decoding data sent from the printer driver 503 by referring to the print mode and the like.

The source code for the printer driver 503 may widely vary as is well known to those skilled in the art. For example, minor modifications may be made to the source code of commercially available printers, such as the HP® 550C, for use in the present invention. One such modification involves the adjustment to the voltages applied to the nozzle gate to account for different electrical resistance values. In this manner, the appropriate amount of the cell composition may be dispensed regardless of concentration, viscosity, or pH. Other software modifications may include repositioning the nozzle to print at the exact same location when addressing a different reservoir. Further, modifications may also be made to provide for temperature control and settings for non-aqueous liquid carriers. In one embodiment, for instance, the heat applied to the reservoir may be adjusted so that the temperature of the drops does not exceed 100° F. Likewise, the software may also be modified to allow collective or independent control of the nozzles. For example, the software may allow the user to control not only the x and y positions of the desired print location, but also the specific nozzles of the printer head to address whether each specific nozzle should be on (printing) or off (not printing) at each location. If desired, instructions may be prepared by entering information into a text data file. Specifically, the software may be devised to read the text data file and assemble it into useful information for the printer, which can then send the printer head to the desired position and activate the proper nozzle over the identified position. For one possible text data file that can be read by a controller, the values of the x position and the y position can be identified in 50 micrometer increments in fields dedicated to each coordinate, and one or more fields can identify a specific nozzle and indicate whether the nozzle is on or off at the identified position. For example, to print a drop from a nozzle labeled with the number "4" at a position of one-quarter of an inch (6,350 micrometers) from the left side of the substrate and one-quarter of an inch from the top of the substrate, the text data file could include the following line: 6350 6350 000100000, with the number "1" in the fourth position of the third field indicating the $4^{th}$ nozzle should be turned on at that coordinate. A graphical interface may be employed to select the desired printing positions and the nozzle. For instance, an interface with a user screen may be used that displays a grid corresponding to the substrate surface. The user may then simply identify grid points to select positions and select the specific nozzle or assemblies that are to be activated at each selected point.

The techniques for printing viable cells in accordance with the present invention may be employed in a wide variety of applications. One such application is the formation of genomic and protein expression libraries. For instance, these libraries typically require high throughput screening of thousands of bacteria cells to identify specific DNA sequences, investigate gene expression, and/or search for differentially expressed genes. Patterns of bacteria cells may also be printed according to the present invention to build biosensors, such as to monitor environmental components and detect toxicological contamination. In addition, artificial chromosome libraries and other cell-based sensors may also be formed. The present invention may also be employed in tissue engineering and even organ production.

The present invention may be better understood with reference to the following examples.

EXAMPLE 1

The ability to print viable bacteria cells onto a substrate was demonstrated. Initially, 1.5 milliliters of a pre-warmed sterilized Trypticase® Soy Agar solution (Beckton Dickinson & Co, Cockeysville, Md.) was poured into a first 35-millimeter Petri dish, and 25 milliliters of the Trypticase® Soy Agar solution was poured into a second 100-mllimeter Petri dish. The first Petri dish contained a sterilized coverslip substrate, while the second Petri dish contained a microscope slide substrate. The solutions were allowed to cool to room temperature, thereby forming a thin gel layer on the substrates. The substrates were individually taped to a piece of paper with double sided tape for feeding to a printer.

E. coli DH5α cells (Gibco-BRL, Life Technologies, Rockville, Md.) were grown overnight at 37° C. on a Trypticase® Soy Agar plate. Two loopfuls of organisms (representing approximately two large colonies) were transferred into a centrifuge tube containing 5 milliliters of sterilized water. The cell concentration in the E. coli solution was determined to be $3\times10^7$ cells per milliliter by the standard plate count method (Benson, H. J., *Microbiological Applications—Laboratory Manual in General Microbiology*, 1998, 7$^{th}$ Ed., Boxton: WCB/McGraw-Hill, p. 89–94). This solution was diluted to different concentrations of bacterial suspensions for subsequent printing. The tubes containing bacterial suspensions were forcefully shaken before printing, in order to break up clumps and ensure good distribution of the bacteria.

A modified Canon® Bubble Jet 2100 printer was used to print the bacteria cells onto the coverslip substrate. The Canon® printer was modified by removing the rubber rolls and removing the center springs, and tightening the remaining springs designed to advance paper.

A modified HP® DeskJet 550C printer was used to print the bacteria cells onto the microscope slide substrate. The HP® printer was modified with gear mount pillars having closer tolerances, which was accomplished by adding a horizontal support, changing the transistor in the circuit to one with higher amplification, and re-entering the horizontal position encoder. Both printers utilized a printer driver to allow different viscosities of solutions to be printed. The printer drivers constantly adjusted the voltages to the nozzles to account for different impedances of the solutions, thus allowing the appropriate amount of solution to be dispensed. The printer drivers are available for download at the following website: http://130.127.152.24.

Microsoft PowerPoint software was used to edit a linear colony array pattern with a 2 drops per millimeter density and 0.13 pt weight (Microsoft® PowerPoint™). A black ink-jet cartridge was emptied of its contents, thoroughly cleaned with a 100% ethanol solution, rinsed using autoclaved water, and dried in a sterilized hood. Thereafter, the cartridge was filled with 1 milliliter of a bacterial printing suspension.

Using the modified HP® Desktop 550C printer, drops of the E. coli suspension were ejected onto an agar-coated glass slide according to a pre-designed colony array pattern. Different dilutions of printing suspensions (1:10, 1:100 and 1:1000 from the original print suspension) were also used. All printed slides were incubated at 37° C. overnight. The E. coli colony arrays were then scanned using an Epson Perfection 1640SU scanner, and the images were recorded for further analysis. The E. coli imprinted agar-coated slides were placed onto a high-resolution scanner after incubation for 20 hours at 37° C. The scanner provided an even light source for the optimal recording of the imprinted colony arrays.

Figure 9:
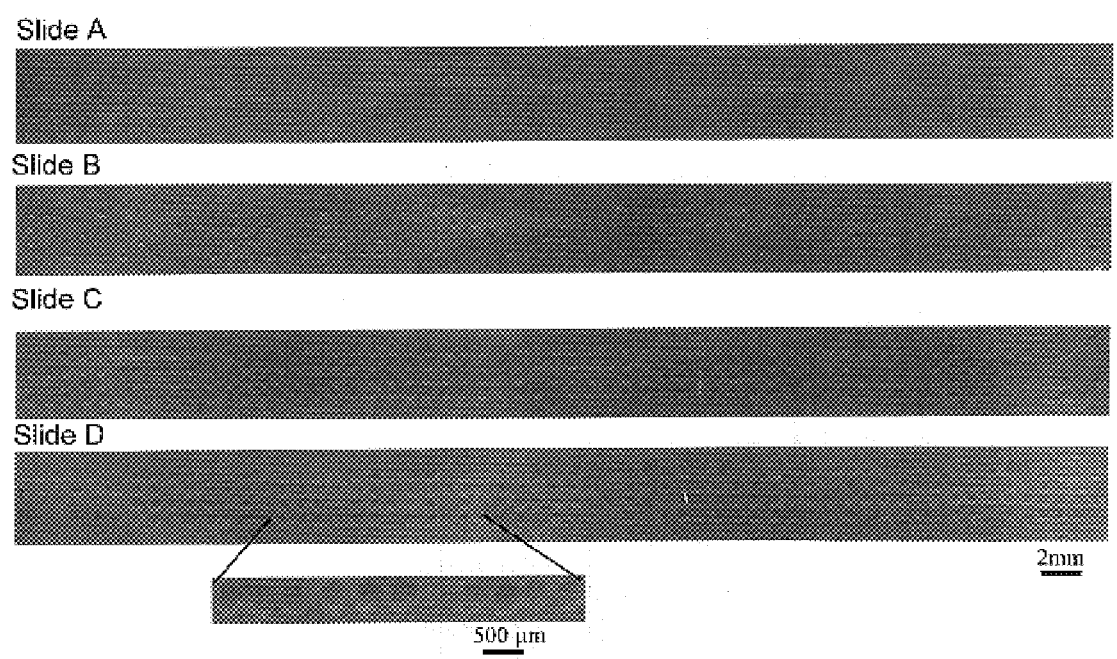
FIG. 9 illustrates optical recordings formed by scanning *E. coli* arrays in Example 1.

FIG. 9 shows the optical recording of colony arrays from different bacterial concentrations printed with the HP® 550C on glass slides with an identically designed pattern. Individual colonies had a circular shape with an approximate diameter of 500 micrometers. Few colonies were observed on slides A and B, where the bacterial print concentrations were $3\times10^4$ and $3\times10^5$ cells per milliliter, respectively. In slides C and D, where the bacterial print concentrations were $3\times10^6$ and $3\times10^7$ cells per milliliter, respectively, the bacterial colonies matched the designed array pattern. Overlapping colonies were observed in the slides with the highest bacterial concentration. Furthermore, it appeared that occasionally, during the nozzle firing, satellite drops formed and resulted in bacterial colonies growing outside the designed pattern (slide D).

Figure 10:
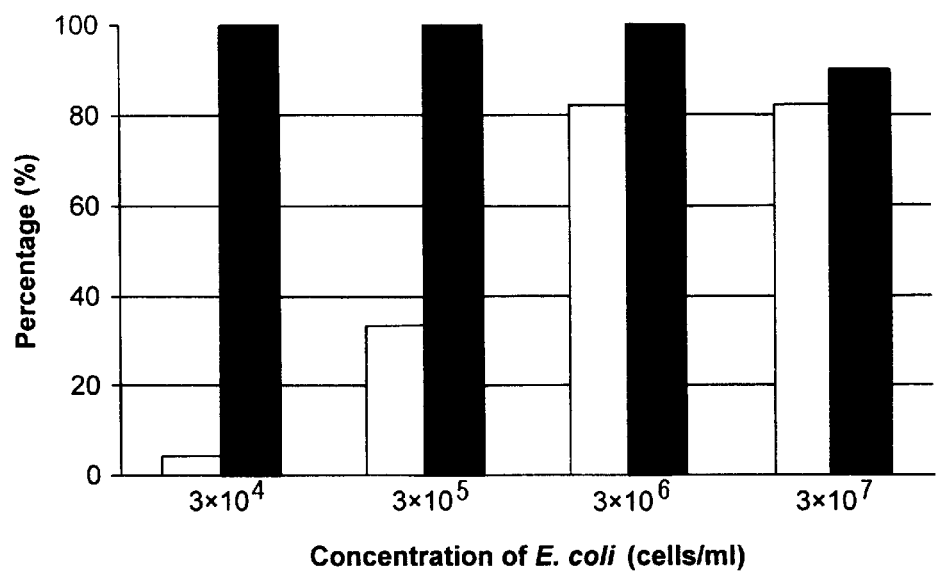
FIG. 10 represents graphically the relative number of printed and isolated colonies in relation to the concentration of printed bacterial suspensions in Example 1.

To analyze the ability to obtain optimal single-colony arrays, the relative number of imprinted dots and isolated colonies were counted on each slide and graphed versus the concentration of the bacterial suspension (FIG. 10). As shown, a bacterial concentration of $3\times10^6$ cells per milliliter resulted in single colony arrays with high fidelity pattern.

Figure 11:
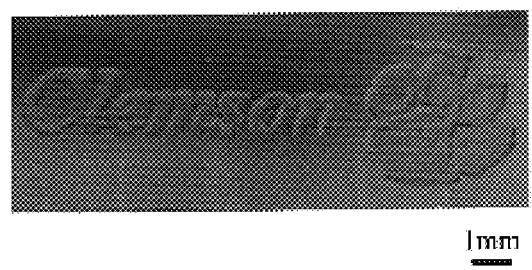
FIG. 11 is a photograph of a complex pattern generated by printing viable *E. coli* cells on a substrate in Example 1.
Figure 12A:
FIG. 12 illustrates a cell density gradient printed according to Example 1.
Figure 12B:
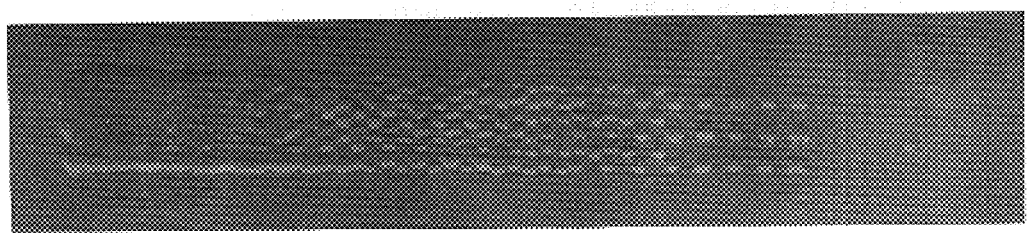

Using the modified Canon® Bubble Jet 2100 printer, a $3\times10^7$ cells per milliliter suspension of E. Coli cells was deposited onto the agar-coated coverslip substrate. The cell suspension was printed with a cartoon tiger paw (FIG. 11) and a black color gradient (FIG. 12). After printing, the cells were incubated at 37° C. overnight. The cartoon tiger paw of FIG. 11 illustrated the ability to print cells in an irregular shape. No obvious visual pattern could be seen by naked eye immediately after printing the E. coli suspension onto the agar substrate. However, after overnight incubation at 37° C., the pattern became visible. The living bacteria thus created the complex image of a tiger paw. The black color gradient of FIG. 12 was designed to represent a continuously changing pattern, where the darkness of color represented the density of printed bacteria cells. FIG. 12 represents the designed gradient pattern and the printed bacterial density gradient after 24 hours of incubation at 37° C. The deposition of cells onto the soy agar surface with the modified Canon® printer following the grayscale pattern showed a bacterial density-gradient that changed from complete coverage, on the left side, to virtually no colonies, on the extreme right, hence closely matching the designed pattern.

EXAMPLE 2

The ability to print mammalian cells onto a substrate was demonstrated. Initially, bovine aortal endothelial cells and a smooth muscle cell line (American Type Culture Collection, ATTC) (passage 10) were trypsinized and resuspended in a modified Eagle's medium (MEM) and 10% fetal bovine serum (FBS), with a concentration of $1\times10^5$ cells per milliliter. The cell suspensions were then printed onto a reconstituted basement membrane gel (Matrigel™, available from Collaborative Biomedical Products of Bedford, Mass.) and a 3 milligram per milliliter collagen gel (available from Elastin Products, Inc., Owensville, Mo.) utilizing a HP® 660C printer that was modified in the same manner as described for the HP® Desktop 550C printer above in Example 1. In addition, a new printer head was installed, similar to that shown in FIG. 2. Specifically, an individually wrapped, sterile 30-gauge needle (Becton Dickinson) was aseptically filled with the cell suspension, and screwed into the printer head. The drops produced by the needle had an average diameter of 0.006 inches or a volume of $1.5 \times 10^{-5}$ milliliters, resulting in an average of 1.5 cells per drop (either one or two cells per drop).

During operation, the printer was placed in a sterile laminar flowhood. Printing was conducted at room temperature and was completed in less than 1 minute per sample. A line was printed by placing each cell in its position along a virtual line. The printed cells were then incubated in 5% $CO_2$ at 37° C. for 30 minutes before an MEM liquid medium was added. After 72 hours of incubation, the cells were visualized with a live/dead assay (Molecular Probes, Inc.) under an epifluorescent microscope (Nikon, Inc, Melville, N.Y.).

FIGS. 13A and 13B show the epifluorescence images obtained following the incubation period. FIG. 13A shows the results of printing the endothelial cells on the Matrigel™ basement membrane gel, and FIG. 13B shows the results of printing the endothelial cells on the collagen gel. The results indicated that the majority of cells stayed alive and attached to their respective positions after printing (e.g., about 75%), with only about 25% of the cells found dead upon inspection of the printed patterns. However, because the drop volumes were small and evaporated quickly under ambient conditions, the cell death was believed to be primarily associated with dehydration of the cells after printing.

EXAMPLE 3

The ability to use a gelling polymer to assist in the printing of cells was demonstrated. Specifically, a poly[N-isopropylacrylamide-co-2-(N,N-dimethylamino)-ethyl acrylate] thermogelling copolymer, denoted henceforth as K-70, was used. The copolymer had a molecular weight of 510 kiloDaltons, as estimated by gel permeation chromatography (GPC) with a light-scattering detector. The polymer synthesis and characterization is as described in *Injectable Gels for Tissue Engineering*, Anat. Rec., by Gutowska, Jeong, and Jasionowski 263:342–349 (2001).

A 10 wt. % solution of the copolymer in cold deionized water was formed, placed into an external ice bath, and stirred magnetically overnight. After the polymer was completely dissolved, the pH of the solution was adjusted to 7.0 with 0.1 M NaOH using pH strips. The polymer solution was sterilized for 30 minutes in an autoclave, cooled, and then re-dissolved. The solution was allowed to become completely clear and mixed well before further use.

The polymer solutions were combined with an equal amount of 2× cell culture medium that included MEM, supplemented with 10% fetal bovine serum (FBS) and 1% antibiotic solution. The final polymer concentration was not lower than 4–5 wt. %. The solution was then divided into sterile stainless steel needles with luer plastic hubs. Care was taken to maintain the needle temperatures below 4° C. to avoid gelling of the polymer. One half of the solutions were dyed by adding 30 microliters of 1% trypan blue dye to each milliliter of polymer solution to better visualize the printed layers.

Collagen gels were prepared according to the method described in *Collagen As a Substrate for Cell Growth and Differentiation*, Methods Enzymol, Strom and Michalopoulous, 82:544–555 (1982), with the exception that lyophilized calfskin collagen was used rather than rat-tail collagen. A 3.3 milligram per milliliter collagen solution was prepared by slowly dissolving the collagen in acetic acid (1%) at 0° C. The gel was prepared by adding 156.5 microliters of sterile, filtered 10×DMEM and 30 microliters of sterile 0.34 N NaOH to each milliliter of collagen solution. The resulting solution was divided into several stainless steel needles with luer plastic hubs and kept on ice until they were used. Care was taken to maintain the needle temperatures below 4° C. to avoid gelling of the polymer.

The modified HP® 660C printer of Example 2 was used to print the gel solutions. A series of drops of the prepared gels were deposited onto heated (36° C.) Petri dishes and the thickness of the gel layers was evaluated. Each drop was allowed to gel before a new, smaller drop was placed on top of the previously deposited drop. The series of staggered gel layers was placed onto a microscope and visualized. The movement (in micrometers) of the microscope objective was measured as the focal plane shifted from one layer to the next. Alternate layers of clear and trypan blue K-70 gel were analyzed under a microscope. FIG. 14 shows a top view of the layered gel. The thickness of the layers varied between about 200 and 500 micrometers. During the addition of the polymer solutions to the already gelled layers, it was clear that only minimal (if any) mixing of the layers occurred. This is believed to have occurred because, in its gelled state, the copolymer is hydrophobic, and thus the liquid solution drops did not spread out on the previously deposited gel.

EXAMPLE 4

Bovine aortal endothelial cells (ATTC, Manassas, Va.) (passage 10) were expanded in T25 culture flasks in the presence of MEM supplemented with 10% FBS and 1% antibiotic solution in a 5% $CO_2$ incubator maintained at 36° C. The media was changed at day 1 and subsequently every other day. After growing to a confluent monolayer, the cells were washed by replacing the media with isotonic phosphate-buffered saline (PBS). They were then incubated in a PBS solution containing a millimolar solution of the tripeptide arginine-glycine-aspartic acid (RGD) and agitated for 30–45 minutes in the incubator. The agitation caused the cells attached to the edges of the flask to dislodge. Further mechanical scraping of the flask with a sterile glass pipette caused the cells to detach in aggregates. The aggregates were collected, centrifuged at 1,000 rpm for 5 minutes, and resuspended in 0.5 milliliters of media. The size of the aggregates was measured as having an average diameter of 540±183 micrometers (the average was computed after 18 trials). The aggregates were then reseeded by hand on both collagen and K-70 gels from in Example 3.

Figure 15A:
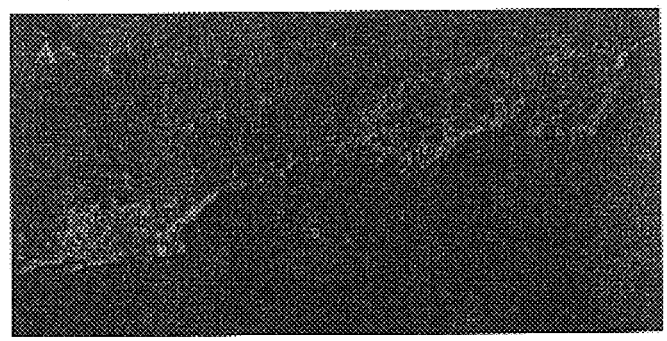
FIGS. 15A and 15B are photographs of cell aggregates following fusion in Example 4.
Figure 15B:
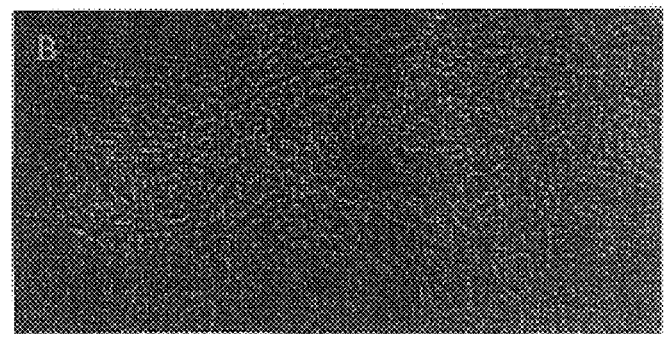

Cell aggregates were placed by hand in close opposition on the surface of collagen type gel. Adjacent cell aggregates fused over time, with a sequential formation of elongated rod-like tissue constructs (FIG. 15A). Similar results were produced when the cell aggregates were placed on the surface of collagen and then sequentially covered with a second collagen layer. This illustrated that fusion of cell aggregates can occur, not only on the surface, but also within 3D collagen gel. Cell aggregates were then placed in close opposition on the surface of the thermo-reversible K-70 gel. Although the overall effectiveness of the thermo-reversible gels in promoting cell aggregate fusion was not equal to that of the collagen gel, fusion did occur in these gels as well, as shown in FIG. 15B.

Figure 16:
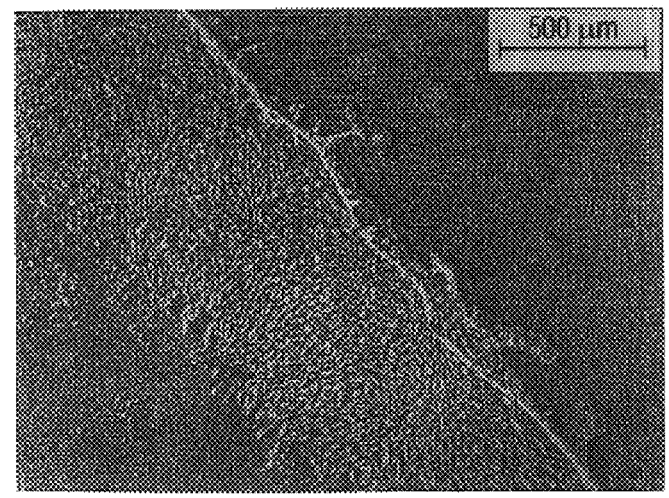
FIG. 16 is a photograph of cell aggregates following fusion on a printed collagen gel ring in Example 4.

Collagen gels were then deposited in ring patterns about 1 centimeter in total diameter and about 500 micrometers wide using the printer. After gelling occurred, the BAEC aggregates were added to the gel by hand. Observation after 24 hours revealed that the cells were spread throughout the gel. A live/dead assay image is shown in FIG. 16. The cells shown within the gel were alive, while most of the cells that migrated out of the gel were dead. The viability of the cells was assessed with a commercially available live/dead assay (Molecular Probes, Inc., Eugene, Oreg.). The samples were rinsed with PBS, and incubated for 30 minutes in a solution of calcein AM and ethidium homodimer-1 in PBS according to the manufacturer's protocol. Fluorescence was observed in an inverted epifluorescent microscope (Nikon Diaphot 300, Nikon, Inc., Melville, N.Y.) using a DAPI/FITC/TRITC triple-band filter.

EXAMPLE 5

The ability to print a three-dimensional array of cells was demonstrated. The array was constructed from two intersecting two-dimensional lines of cells.

Initially, a syringe was filled with the collagen solution of Example 3 and green-fluorescent protein (GFP) transfected CHO cells suspended in MEM at a concentration of $1 \times 10^6$ cells/ml. The pH of this mixture was about 6.8, and the temperature was maintained at 4° C.

10 gm/liter of a Type II agarose solution in water (available from Sigma Chemical Inc.) was maintained at 80° C. and filled into a second syringe. Both syringes were mounted into the printer head of the modified HP® 660C printer described in Example 2. A layer of the agarose solution was then printed from the syringe in a series of drops as described in Example 3. The gel layer was evaluated after cooling as in Example 3.

Figure 17:
FIG. 17 is a microscopic photograph of the cell layers printed in Example 5.
Figure 18A:
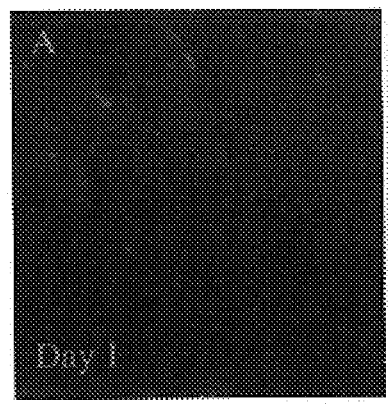
FIG. 18 is a photograph of printed cells over the course of 15 days of development in Example 6.
Figure 18B:
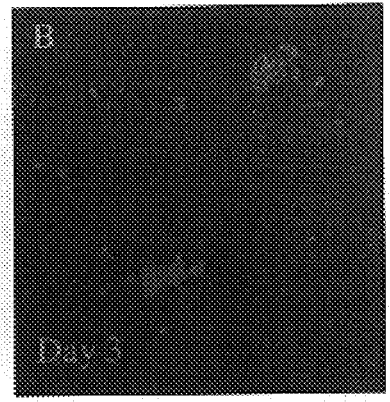
Figure 18C:
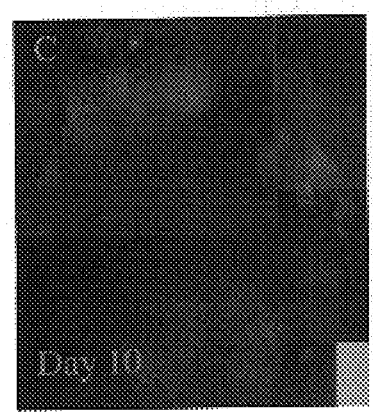
Figure 18D:
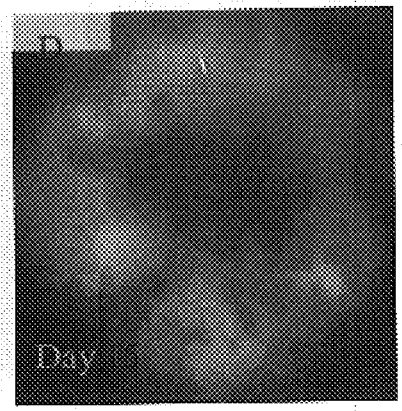

The collagen/cell solution was then printed out of the other syringe as the printer head moved in a linear fashion, thus depositing a two-dimensional line of cells and collagen onto the printed agarose solution. This deposition occurred as described in Example 3, with the exception that the cells were pre-mixed with the collagen. The line was 3 millimeters long and 500 microns wide. The printer head was then held stationary while the substrate was moved under the printer head, and a second line of cells and collagen was printed perpendicular to the first line. The second line was also 3 millimeters long and 500 microns wide. The samples were rinsed with PBS, and incubated for 24 hours in MEM media. Fluorescence was observed after 24 hours in an inverted epifluorescent microscope (Nikon Diaphot 300, Nikon, Inc., Melville, N.Y.) using a GFP band filter. A microscopic image of the results is shown in FIG. 17. The layered cellular structure is shown in FIG. 17 where the two intersecting lines of viable cells cross each other.

EXAMPLE 6

The ability to print viable mammalians cells onto a substrate was demonstrated. Chinese Hamster Ovary (CHO) cells were cultured and prepared for printing onto a semi-solid agar medium. A Hewlett Packard (HP) 51626a ink cartridge was emptied of ink and prepared as described above in Example 1. The CHO cells employed were transfected with green fluorescence protein (GFP) genes, to facilitate the visualization of the patterns with an epifluorescent microscope. The cells were cultured with Dulbecco's modified Eagle's medium (DMEM) (Sigma Chemical Inc, St. Louis, Mo.) for nourishment and kept in an incubator at a constant temperature of 37° C. A semi-solid agar medium was then prepared by combining a solution of soy agar and a 2× concentrated solution of DMEM. The soy agar was prepared by dissolving 1.5 grams of powdered trypticase soy agar in 50 milliliters of nanopure water and autoclaving for 15 minutes to sterilize and further dissolve the agar. While the soy agar was still a hot liquid, it was combined with 50 milliliters of a 2× concentration DMEM solution. The semi-solid agar medium was then transferred into 35-millimeter petri dishes each containing one sterile cover slip. The semi-solid agar medium was then cooled to form a gel-like sheet.

The CHO cells were removed from their flasks by trypsinization. After detachment, the cells and trypsin were combined with a solution of DMEM augmented by 10% fetal bovine serum (FBS), sodium bicarbonate, and 1% antibiotic/antimycotic. The combined solution was centrifuged, and thereafter, the supernatant was aspirated. The cells were resuspended in 1 milliliter of Dulbecco's phosphate buffered saline solution (PBS) (4× concentration). Once immersed in this hypertonic solution, the CHO cells shrunk by osmosis and became small enough to pass through the printer head without clogging the orifice.

The CHO cells were then printed utilizing the HP® 660C printer modified in the same manner as described above in Example 2. Initially, cover slips coated with the semi-solid agar medium were cut out of the petri dishes and arranged on the printer in the path below the printer head. A portion of the cell solution was pipetted into the nozzle of the ink cartridge, and the cartridge was placed back into the printer. The cell solution was printed onto the cover slips in a circular pattern. After printing, the cover slips were transferred into 35-millimeter petri dishes and incubated at 37° C.

The results of the printing process are shown in FIG. 18. For instance, referring to FIG. 18A, some of the cells were immediately visible on the gel, although at this point, there did not appear to be a specific predefined circular printed shape. However, subsequent viewing under the epifluorescent microscope suggested that the cells started to divide and occupy the pre-designed shape on Day 3 (FIG. 18B). This is even more evident on Day 10 (FIG. 18C) and Day 15 (FIG. 18D), where the cells clearly divided and fused into a thick circular tissue.

EXAMPLE 7

The ability to print a three-dimensional array of cells was demonstrated. The CHO cells of Example 6 were resuspended in 0.5 molar solution of a calcium chloride solution and methylene blue dye. The cell solution was then printed using an HP® 694C printer modified in the same manner as described for the HP® Desktop 550C printer and using a vertical translation stage as described herein and shown in FIG. 20. Specifically, a standard ink cartridge was initially filled with the cell solution as described in Example 6. Hybond N+ blotting membranes were wetted with a 1% alginic acid solution dissolved in PBS, and placed onto the surface of the stage, which was held at its highest position.

Figure 19:
FIG. 19 is a photograph of three dimensional cylinders of viable cells structurally supported by a chemically crosslinked hydrogel in Example 7.

A paper substrate was "primed" by printing the CHO solution from the ink cartridge in the desired circular shape. The CHO solution was printed five times, each on top of the previous printing. A small amount of alginic acid solution was manually placed over the primed area, causing the alginic acid to gel and form a gel base on the surface of the membrane. The chamber was then filled with alginic acid until the surface of the stage was just covered with the liquid. The circular pattern was printed three times, and the chemically crosslinked hydrogel was formed on the stage. The stage was moved downwards slightly until the hydrogel was positioned slightly below the surface of the liquid. The process of printing and lowering the stage was repeated and a solid tube comprising CHO cells within the chemically crosslinked hydrogel material was formed. FIG. 19 shows 4 cylinders printed simultaneously in this manner.

These and other modifications and variations of the present invention may be practiced by those of ordinary skill in the art, without departing from the spirit and scope of the present invention, which is set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A method for forming an array of viable cells, said method comprising ink-jet printing a cellular composition containing cells onto a substrate, wherein at least about 25% of said cells remain viable on said substrate after incubation for 24 hours at 37° C. in a 5% $CO_2$/95% $O_2$ environment.

2. A method as defined in claim 1, wherein an ink-jet printer containing at least one printer head is used to print said cellular composition onto said substrate.

3. A method as defined in claim 2, wherein said printer head defines at least one orifice through which said cellular composition is capable of flowing.

4. A method as defined in claim 3, wherein said orifice is positioned from about 0.1 to about 30 millimeters from said substrate.

5. A method as defined in claim 3, wherein said orifice is positioned from about 0.5 to about 3 millimeters from said substrate.

6. A method as defined in claim 3, wherein said orifice has a size sufficient to inhibit substantial clogging of said cellular composition within said printer head.

7. A method as defined in claim 2, wherein a pressurization actuator facilitates the formation of a droplet of said cellular composition.

8. A method as defined in claim 7, wherein said pressurization actuator receives a voltage pulse ranging from about 1 to about 50 volts.

9. A method as defined in claim 7, wherein said pressurization actuator receives a voltage pulse ranging from about 10 to about 20 volts.

10. A method as defined in claim 7, wherein said pressurization actuator is selected from the group consisting of piezoelectric crystals, acoustic devices, thermal devices, and combinations thereof.

11. A method as defined in claim 1, wherein said cellular composition contains procaryotic cells.

12. A method as defined in claim 1, wherein said cellular composition contains eucaryotic cells.

13. A method as defined in claim 1, wherein said cellular composition contains cell aggregates.

14. A method as defined in claim 1, wherein the concentration of said cells within said cellular composition is from about $1 \times 10^3$ to about $1 \times 10^{16}$ cells per milliliter.

15. A method as defined in claim 1, wherein the concentration of said cells within said cellular composition is from about $3 \times 10^5$ to about $1 \times 10^9$ cells per milliliter.

16. A method as defined in claim 1, further comprising depositing a support compound onto said substrate.

17. A method as defined in claim 16, wherein said support compound is a gel or a compound capable of forming a gel.

18. A method as defined in claim 17, wherein said support compound forms a gel after being deposited onto said substrate.

19. A method as defined in claim 17, wherein said support compound is crosslinked after being deposited onto said substrate.

20. A method as defined in claim 19, wherein the crosslinking is induced by immersing said substrate into a solution containing said support compound or a crosslinking agent for said support compound.

21. A method as defined in claim 16, wherein said support compound is printed onto said substrate.

22. A method as defined in claim 21, wherein said support compound is mixed with said cellular composition prior to being printed onto said substrate.

23. A method as defined in claim 16, wherein said support compound is selected from the group consisting of agar, collagen, hydrogel polymers, and combinations thereof.

24. A method as defined in claim 1, wherein a two-dimensional array of said cells is formed on said substrate.

25. A method as defined in claim 1, wherein a three-dimensional array of said cells is formed on said substrate.

26. A method as defined in claim 1, further comprising ink-jet printing multiple droplets of said cellular composition onto said substrate.

27. A method as defined in claim 26, wherein said multiple droplets fuse into a cohesive cellular assembly.

28. A method as defined in claim 26, wherein said multiple droplets are printed in multiple printing passes.

29. A method as defined in claim 1, wherein at least about 50% of said cells remain viable on said substrate after incubation for 24 hours at 37° C. in a 5% $CO_2$/95% $O_2$ environment.

30. A method as defined in claim 1, wherein at least about 75% of said cells remain viable on said substrate after incubation for 24 hours at 37° C. in a 5% $CO_2$/95% $O_2$ environment.

31. A method as defined in claim 1, wherein at least about 85% of said cells remain viable on said substrate after incubation for 24 hours at 37° C. in a 5% $CO_2$/95% $O_2$ environment.

32. A method as defined in claim 1, wherein the density of said cells on said substrate is from about 0.1 to about 2 cells per square millimeter.

33. A method as defined in claim 32, wherein the density of said cells on said substrate is from about 0.25 to about 1 cell per square millimeter.

34. A method as defined in claim 1, wherein the density of said cells on said substrate is from about 0.0001 to about 1 cell per square micrometer.

35. A method as defined in claim 34, wherein the density of said cells on said substrate is from about 0.0004 to about 0.25 cells per square micrometer.

36. A method for forming an array of viable cells, said method comprising:
   supplying a cellular composition containing cells to at least one printer head of an ink-jet printer, said printer head defining an orifice through which said cellular composition is capable of flowing;
   forming one or more droplets from said cellular composition;
   flowing the droplets through said orifice so that said cells are printed onto a substrate; and
   depositing a support compound onto said substrate for supporting said cells, said support compound forming a gel after being deposited onto said substrate.

37. A method as defined in claim 36, wherein said cellular composition contains eucaryotic cells, procaryotic cells, or combinations thereof.

38. A method as defined in claim 36, wherein said support compound is crosslinked after being deposited onto said substrate.

39. A method as defined in claim 38, wherein the crosslinking is induced by immersing said substrate into a solution containing said support compound or a crosslinking agent for said support compound.

40. A method as defined in claim 36, wherein said support compound is printed onto said substrate.

41. A method as defined in claim 40, wherein said support compound is mixed with said cellular composition prior to being printed onto said substrate.

42. A method as defined in claim 36, wherein said support compound is selected from the group consisting of agar, collagen, hydrogel polymers, and combinations thereof.

43. A method as defined in claim 36, wherein a two-dimensional array of said cells is formed on said substrate.

44. A method as defined in claim 36, wherein a three-dimensional array of said cells is formed on said substrate.

45. A method as defined in claim 36, wherein multiple droplets are printed onto said substrate.

46. A method as defined in claim 45, wherein said multiple droplets fuse into a cohesive cellular assembly.

47. A method as defined in claim 36, wherein at least about 25% of said cells remain viable on said substrate after incubation for 24 hours at 37° C. in a 5% $CO_2$/95% $O_2$ environment.

48. A method as defined in claim 36, wherein at least about 50% of said cells remain viable on said substrate after incubation for 24 hours at 37° C. in a 5% $CO_2$/95% $O_2$ environment.

49. A method as defined in claim 36, wherein at least about 75% of said cells remain viable on said substrate after incubation for 24 hours at 37° C. in a 5% $CO_2$/95% $O_2$ environment.

50. A method as defined in claim 36, wherein at least about 85% of said cells remain viable on said substrate after incubation for 24 hours at 37° C. in a 5% $CO_2$/95% $O_2$ environment.

51. A method as defined in claim 36, wherein the density of said cells on said substrate is from about 0.1 to about 2 cells per square millimeter.

52. A method as defined in claim 36, wherein the density of said cells on said substrate is from about 0.0001 to about 1 cell per square micrometer.

53. An array formed on a substrate from viable printed cells, wherein a gel provides structural support for said viable printed cells, wherein the density of said cells when printed is from about 0.0001 to about 1 cell per square micrometer.

54. An array as defined in claim 53, wherein said gel is crosslinked.

55. An array as defined in claim 53, wherein said gel is selected from the group consisting of agar, collagen, hydrogel polymers, and combinations thereof.

56. An array as defined in claim 53, wherein at least about 50% of said cells remain viable after incubation for 24 hours at 37° C. in a 5% $CO_2$/95% $O_2$ environment.

57. An array as defined in claim 53, wherein at least about 75% of said cells remain viable after incubation for 24 hours at 37° C. in a 5% $CO_2$/95% $O_2$ environment.

58. An array as defined in claim 53, wherein at least about 85% of said cells remain viable after incubation for 24 hours at 37° C. in a 5% $CO_2$/95% $O_2$ environment.

59. An array as defined in claim 53 wherein the density of said cells when printed is from about 0.0004 to about 0.25 cells per square millimeter.

60. An array as defined in claim 53, wherein said cells comprise procaryotic cells.

61. An array as defined in claim 53, wherein said cells comprise eucaryotic cells.

62. An array as defined in claim 53, wherein the array comprises cells of more than one cell type.

63. An array as defined in claim 53, wherein the array is two-dimensional.

64. An array as defined in claim 53, wherein the array is three-dimensional.

65. An array as defined in claim 53, wherein the printed cells form a cohesive cellular assembly.

66. An array as defined in claim 53, wherein the density of said cells when printed varies across at least a portion of the array.

67. An ink-jet printer configured to deposit viable cells onto a substrate, said printer comprising:
 a reservoir for containing the cells;
 a printer head in fluid communication with said reservoir, said printer head defining an orifice having a size of from about 2 to about 200 micrometers, wherein the cells are capable of flowing through said orifice without substantial clogging; and
 a pressurization actuator that is capable of facilitating the formation of a droplet containing the cells for flowing through said orifice, wherein said pressurization actuator receives a voltage pulse that is sufficiently low to facilitate the survival of the cells.

68. An ink-jet printer as defined in claim 67, wherein said voltage pulse ranges from about 1 to about 50 volts.

69. An ink-jet printer as defined in claim 67, wherein said voltage pulse ranges from about 10 to about 20 volts.

70. An ink-jet printer as defined in claim 67, wherein said pressurization actuator is selected from the group consisting of piezoelectric crystals, acoustic devices, thermal devices, and combinations thereof.

71. An ink-jet printer as defined in claim 67, wherein said printer head is moveable in an −x direction.

72. An ink-jet printer as defined in claim 67, further comprising a feed mechanism for receiving the substrate.

73. An ink-jet printer as defined in claim 72, wherein said feed mechanism is configured to move the substrate in a −y direction.

74. A method for forming an array of viable cells, said method comprising:
 supplying a cellular composition containing cells to at least one printer head of an ink-jet printer, said printer head defining an orifice through which said cellular composition is capable of flowing;
 forming one or more droplets from said cellular composition;
 flowing the droplets through said orifice so that said cells are printed onto a substrate; and
 depositing a support compound onto said substrate for supporting said cells, said support compound including a gel or a compound capable of forming a gel, wherein at least about 25% of said cells remain viable on said substrate after incubation for 24 hours at 37° C. in a 5% $CO_2$/95% $O_2$ environment.

75. A method as defined in claim 74, wherein said cellular composition contains eucaryotic cells, procaryotic cells, or combinations thereof.

76. A method as defined in claim 74, wherein said support compound forms a gel after being deposited onto said substrate.

77. A method as defined in claim 74, wherein said support compound is crosslinked after being deposited onto said substrate.

78. A method as defined in claim 77, wherein the crosslinking is induced by immersing said substrate into a solution containing said support compound or a crosslinking agent for said support compound.

79. A method as defined in claim 74, wherein said support compound is printed onto said substrate.

80. A method as defined in claim 79, wherein said support compound is mixed with said cellular composition prior to being printed onto said substrate.

81. A method as defined in claim 74, wherein said support compound is selected from the group consisting of agar, collagen, hydrogel polymers, and combinations thereof.

82. A method as defined in claim 74, wherein a two-dimensional array of said cells is formed on said substrate.

83. A method as defined in claim 74, wherein a three-dimensional array of said cells is formed on said substrate.

84. A method as defined in claim 74, wherein multiple droplets are printed onto said substrate.

85. A method as defined in claim 84, wherein said multiple droplets fuse into a cohesive cellular assembly.

86. A method as defined in claim 74, wherein at least about 50% of said cells remain viable on said substrate after incubation for 24 hours at 37° C. in a 5% $CO_2$/95% $O_2$ environment.

87. A method as defined in claim 74, wherein at least about 75% of said cells remain viable on said substrate after incubation for 24 hours at 37° C. in a 5% $CO_2$/95% $O_2$ environment.

88. A method as defined in claim 74, wherein at least about 85% of said cells remain viable on said substrate after incubation for 24 hours at 37° C. in a 5% $CO_2$/95% $O_2$ environment.

89. A method as defined in claim 74, wherein the density of said cells on said substrate is from about 0.1 to about 2 cells per square millimeter.

90. A method as defined in claim 74, wherein the density of said cells on said substrate is from about 0.0001 to about 1 cell per square micrometer.

* * * * *